US010517997B1

(12) United States Patent
Ostrowski et al.

(10) Patent No.: US 10,517,997 B1
(45) Date of Patent: Dec. 31, 2019

(54) MATERIALS AND METHODS USING FE3+ COORDINATION TO CARBOXYLATES

(71) Applicant: Bowling Green State University, Bowling Green, OH (US)

(72) Inventors: Alexis Ostrowski, Maumee, OH (US); Giuseppe Giammanco, Bowling Green, OH (US)

(73) Assignee: Bowling Green State University, Bowling Green, OH (US)

( * ) Notice: Subject to any disclaimer, the term of this patent is extended or adjusted under 35 U.S.C. 154(b) by 0 days.

(21) Appl. No.: 15/212,233

(22) Filed: Jul. 16, 2016

Related U.S. Application Data

(60) Provisional application No. 62/193,522, filed on Jul. 16, 2015.

(51) Int. Cl.
A61L 27/52 (2006.01)
A61L 27/04 (2006.01)
A61L 27/26 (2006.01)
C12N 5/00 (2006.01)

(52) U.S. Cl.
CPC ............. A61L 27/52 (2013.01); A61L 27/04 (2013.01); A61L 27/26 (2013.01); C12N 5/0068 (2013.01); A61L 2400/18 (2013.01); A61L 2430/34 (2013.01); C12N 2533/74 (2013.01); C12N 2535/00 (2013.01)

(58) Field of Classification Search
None
See application file for complete search history.

(56) References Cited

U.S. PATENT DOCUMENTS

2012/0100210 A1* 4/2012 Draget ............... A61K 9/286 424/463

FOREIGN PATENT DOCUMENTS

CN 103396562 A * 11/2013

OTHER PUBLICATIONS

Narayanan et al. Biomacromolecules (2012) 13: 2465-2471 (Year: 2012).*
Bruchet et al. Processes (2013) 1: 153-166 (Year: 2013).*
Li et al. Adv. Functional Materials (2012) 23: 660-672 (Year: 2012).*
Machine translation of CN 103396562 A (published Nov. 20, 2013) downloaded from ProQuest Mar. 18, 2018 (Year: 2013).*
Rossow et al. Macromolecular Rapid Comm. (2013) 34: 1401-1407 (Year: 2013).*
Giammanco et al. Appl. Mater. Interfaces (2016; published May 25, 2016) 8: 14423-14429 (Year: 2016).*
Bruchet et al. Carbohydrate Polymers (2015; published online May 27, 2015) 131: 57-64) (Year: 2015).*

Tse, J. R.; Engler, A. J. Stiffness Gradients Mimick-ing In Vivo Tissue Variation Regulate Mesenchymal Stem Cell Fate. PLoS ONE 2011, 6, e15978.
Wang, H.; Leinwand, L. A.; Anseth, K S. Cardiac Valve Cells and Their Microenvironment-insights from in Vitro Studies. Nat Rev Cardiol 2014, 11, 715-727.
Vincent, L. G.; Choi, Y. S.; Alonso-Latorre, B.; del Álamo, J. C.; Engler, A. J. Mesenchymal Stem Cell Durotaxis Depends on Sub-strate Stiffness Gradient Strength. Biotechnol. J. 2013, 8, 472-484.
Tokuda, E. Y.; Leight, J. L.; Anseth, K. S. Modulation of Matrix Elasticity with PEG Hydrogels to Study Melanoma Drug Responsiveness. Biomaterials 2014, 35, 4310-4318.
Wang, P.-Y.; Tsai, W.-B.; Voelcker, N. H. Screening of Rat Mesenchymal Stem Cell Behaviour on Polydime-thylsiloxane Stiffness Gradients. Acta Biomater. 2012, 8, 519-530.
Tse, J. R.; Engler, A. J. Preparation of Hydrogel Sub-strates with Tunable Mechanical Properties. In Current Proto-cols in Cell Biology; Bonifacino, J. S.; Dasso, M.; Harford, J. B.; Lippincott-Schwartz, J.; Yamada, K M., Eds.; John Wiley & Sons, Inc.: Hoboken, NJ, USA, 2010.
Trappmann, B.; Gautrot, J. E.; Connelly, J. T.; Strange, D. G. T.; Li, Y.; Oyen, M. L.; Cohen Stuart, M. A.; Boehm, H.; Li, B.; Vogel, V.; et al. Extracellular-Matrix Tethering Regulates Stem-Cell Fate. Nat. Mater. 2012, 11, 642-649.
Sunyer, R.; Jin, A. J.; Nossal, R.; Sackett, D. L. Fabri-cation of Hydrogels with Steep Stiffness Gradients for Study-ing Cell Mechanical Response. PLoS ONE 2012, 7, e46107.
Tripathy, T.; Pandey, S. R.; Karmakar, N. C.; Bhagat, R. P.; Singh, R. P. Novel Flocculating Agent Based on Sodium Alginate and Acrylamide. Eur. Polym. J. 1999, 35, 2057-2072.
He, S.; Ren, B.; Liu, X.; Tong, Z. Reversible Electro-gelation in Poly(acrylic Acid) Aqueous Solutions Triggered by Redox Reactions of Counterions. Macromol. Chem. Phys. 2010, 211, 2497-2502.
Auletta, J. T.; LeDonne, G. J.; Gronborg, K. C.; Ladd, C. D.; Liu, H.; Clark, W. W.; Meyer, T. Y. Stimuli-Responsive Iron-Cross-Linked Hydrogels That Undergo Redox-Driven Switching between Hard and Soft States. Macromolecules 2015, 48, 1736-1747.
Kulkarni, R. V.; Boppana, R.; Krishna Mohan, G.; Mu-talik, S.; Kalyane, N. V. pH-Responsive Interpenetrating Net-work Hydrogel Beads of Poly(acrylamide)-G-Carrageenan and Sodium Alginate for Intestinal Targeted Drug Delivery: Synthesis, in Vitro and in Vivo Evaluation. J. Colloid Interface Sci. 2012, 367, 509-517.
Maia, A. M. S.; Silva, H. V. M.; Curti, P. S.; Balaban, R. C. Study of the Reaction of Grafting Acrylamide onto Xanthan Gum. Carbohydr. Polym. 2012, 90, 778-783.
Woodrow, J. E.; Seiber, J. N.; Miller, G. C. Acrylamide Release Resulting from Sunlight Irradiation of Aqueous Poly-acrylamide/Iron Mixtures. J. Agric. Food Chem. 2008, 56, 2773-2779.

(Continued)

Primary Examiner — Susan M Hanley
(74) Attorney, Agent, or Firm — MacMillan, Sobanski & Todd, LLC

(57) ABSTRACT

Uronate-containing polysaccharide hydrogels that can be photo-patterned are described. The method involves forming a hydrogel and imetal-coordinating it with a reducible metallic cation and exposing the hydrogel to light in a desired pattern. The exposure to light reduces the metallic cation and results in an irreversible change in the elastic moduli and pore size of the irradiated portions of the patterned hydrogel. The method aha the benefit of allowing the user to produce such a hydrogel in any pattern desired. Patterned hydrogels and cell substrates formed by this method are also described.

11 Claims, 24 Drawing Sheets

Specification includes a Sequence Listing.

(56) References Cited

OTHER PUBLICATIONS

Leal D.; Matsuhiro, B.; Rossi, M.; Caruso, F. FT-IR Spectra of Alginic Acid Block Fractions in Three Species of Brown Seaweeds. Carbohydr. Res. 2008, 343, 308-316.

Drury, J. L.; Mooney, D. J. Hydrogels for Tissue Engineering: Scaffold Design Variables and Applications. Biomaterials 2003, 24, 4337-4351.

Engler, A. J.; Griffin, M. A.; Sen, S.; Bonnemann, C. G.; Sweeney, H. L.; Discher, D. E. Myotubes Differentiate Optimally on Substrates with Tissue-like Stiffness: Pathological Implications for Soft or Stiff Microenvironments. J. Cell Biol. 2004, 166, 877-887.

Lee J.; Abdeen, A. A.; Zhang, D.; Kilian, K. A. Directing Stem Cell Fate on Hydrogel Substrates by Controlling Cell Geometry, Matrix Mechanics and Adhesion Ligand Composition. Biomaterials 2013, 34, 8140-8148.

Discher, D. E.; Janmey, P.; Wang, Y. Tissue Cells Feel and Respond to the Stiffness of Their Substrate. Science 2005, 310, 1139-1143.

Engler, A. J.; Sen, S.; Sweeney, H. L.; Discher, D. E. Matrix Elasticity Directs Stem Cell Lineage Specification. Cell 2006, 126, 677-689.

Annabi, N.; Nichol, J. W.; Zhong, X.; Ji, C.; Koshy, S.; Khademhosseini, A.; Dehghani, F. Controlling the Porosity and Microarchitecture of Hydrogels for Tissue Engineering. Tissue Eng. Part B Rev. 2010, 16, 371-383.

\* cited by examiner

Alginate (Alg)
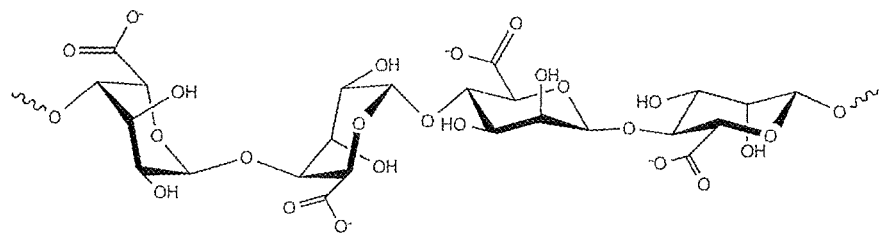
[α–D–guluronic acid][α–D–guluronic acid][β–D–manuronic acid acid][β–D–manuronic acid acid]
Pectate (Pec)
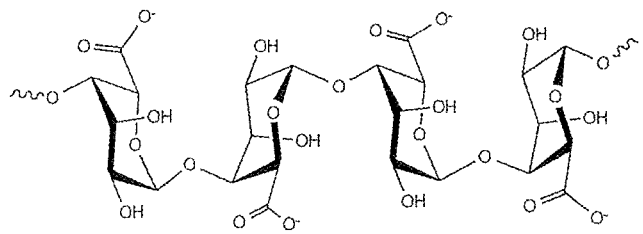
[α–D–galacturonic acid][α–D–galacturonic acid][α–D–galacturonic acid][α–D–galacturonic acid]
Hyaluronate (Hya)
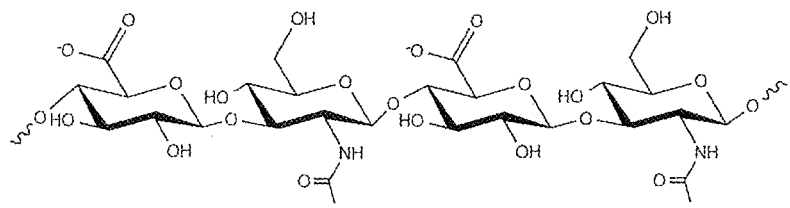
[β–D–glucuronic acid][N-acetyl-β–D–glucosamine][β–D–glucuronic acid][N-acetyl-β–D–glucosamine]
FIGURE 1
PRIOR ART

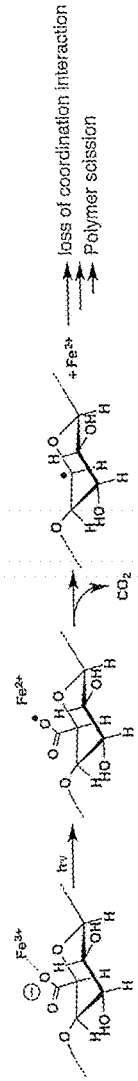
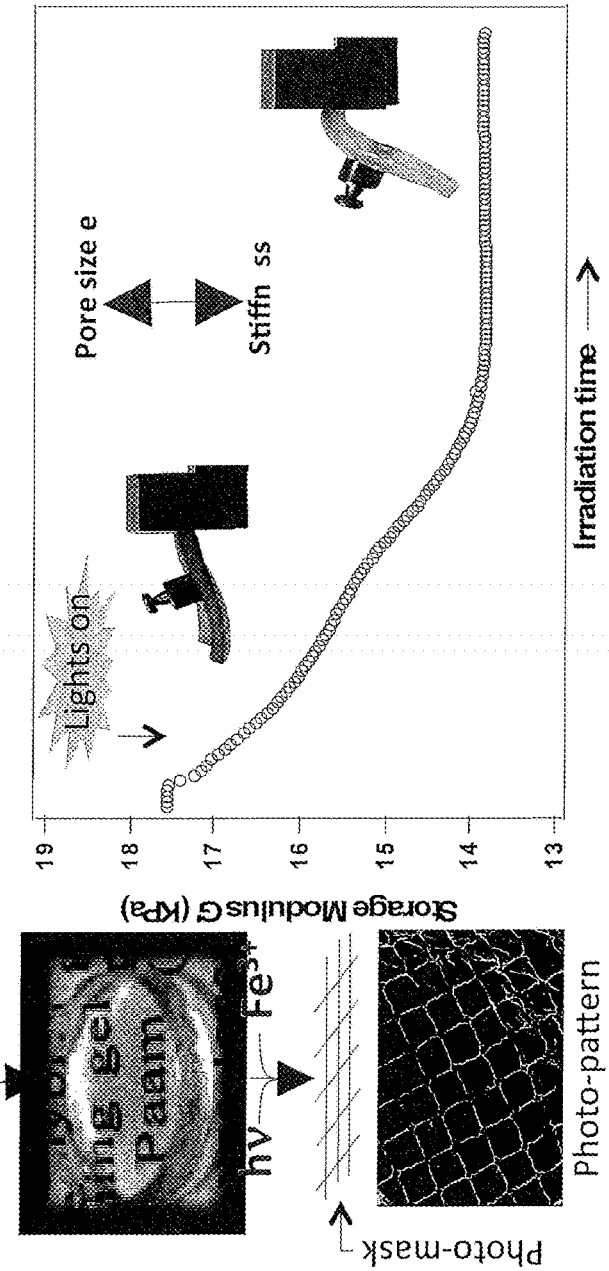
FIGURE 2

MATERIALS AND METHODS USING FE3+ COORDINATION TO CARBOXYLATES

SEQUENCE LISTING

The instant application contains a Sequence Listing which has been filed electronically in ASCII format and is hereby incorporated by reference in its entirety. The ASCII copy, created on Aug. 28, 2019, is named 61104-US-NP_SL.txt and is 516 bytes in size.

FIELD OF THE INVENTION

The present invention relates to creation of photo-patterned hydrogels. In specific embodiments, the hydrogels comprise uronate-containing polysaccharide. In embodiments, the hydrogels are photo-patterned after impregnation with metallic cations.

BACKGROUND OF THE INVENTION

Substrate materials are an essential element in tissue engineering, where the chemical and physical properties of the support matrix can ultimately control the fate and viability of the growing cells.[1-4] Bio-materials for applications in regenerative medicine need to offer easy ways to modify and tune these properties in order to control the interactions of the substrate material with the growing tissue. Most materials used for tissue engineering and cell culture present uniform mechanical properties. However, in vivo, cells may find dynamic changes in the stiffness of the extracellular matrix at the interface of different tissues or as a consequence of disease states.[5,6] The elasticity of substrate materials creates mechanical cues for the development of the growing cells.[1,5,7]

These cues have been widely studied using model systems such as polyacrylamide (Paam) gels, where the stiffness can be controlled by[5,6,7,8] adjusting the ratio of reagents during the formulation[1,8-10] or performing uneven, or multi-step polymerization of the substrate with different intensities of light or heat.[1,3,8,5,11] However, none of these approaches offer a post-synthetic alternative for tuning and controlling the mechanical properties of the substrate. Described herein is a facile method for the photo-patterning of already prepared hydrogel materials to create gradients and interfaces in stiffness and elasticity. By patterning these materials, mechanical cues to control and direct the development of cells can be created.

SUMMARY OF THE INVENTION

The present invention is directed toward a method of creating patterns on a hydrogel by forming a hydrogel; exposing the hydrogel to a metallic cation that can be reduced, thereby creating a metal-coordinated hydrogel; irradiating at least a portion of the metal-coordinated hydrogel causing a reduction of the metallic cation to form a reduced metallic cation in the portion irradiated, thereby creating a patterned hydrogel; and rinsing the patterned hydrogel to remove the reduced metallic cation. The patterns created are based on which portion of the metal-coordinated hydrogel are irradiated and wherein the patterns created involve variations in elastic moduli and pore size. The irradiated portion of the patterned hydrogel have reduced elastic moduli and have greater pore size than a non-irradiated portion of the patterned hydrogel.

The method can be used to form cell substrates for cell growth or cell differentiation. The invention also includes hydrogels formed by the method described. Also included are hydrogels with a first and a second area in a pattern, where the second area exhibits a greater elastic moduli and greater pore size then the first area and a hydrogel having a first phase and a second phase, where in the first phase the hydrogel is non-irradiated and is metal-coordinated with a metallic cation that can be reduced and wherein in the second phase, the hydrogel has been irradiated and the metallic cation that can be reduced is in a reduced form.

BRIEF DESCRIPTION OF THE DRAWINGS

The above, as well as other advantages of the present invention, will become readily apparent to those skilled in the art from the following detailed description when considered in the light of the accompanying drawings in which:

FIG. 1 shows a sampling of known chemical structures of the different uronate containing polysaccharides (UCPS) used to create hybrid polyacrylamide gels.

FIG. 2 shows a chemical schematic (A) and a graphic (B) of photo-induced degradation of Fe(III)-UCPS to induce of loss of the coordination crosslinking and degradation of the polysaccharide in accordance with an embodiment of the invention.

FIG. 19 shows SEM micrographs showing differences in the microstructure of hydrogels produced in accordance with an embodiment of the invention and their corresponding pore size distribution histograms

SEQUENCE LISTING

Figure 3:
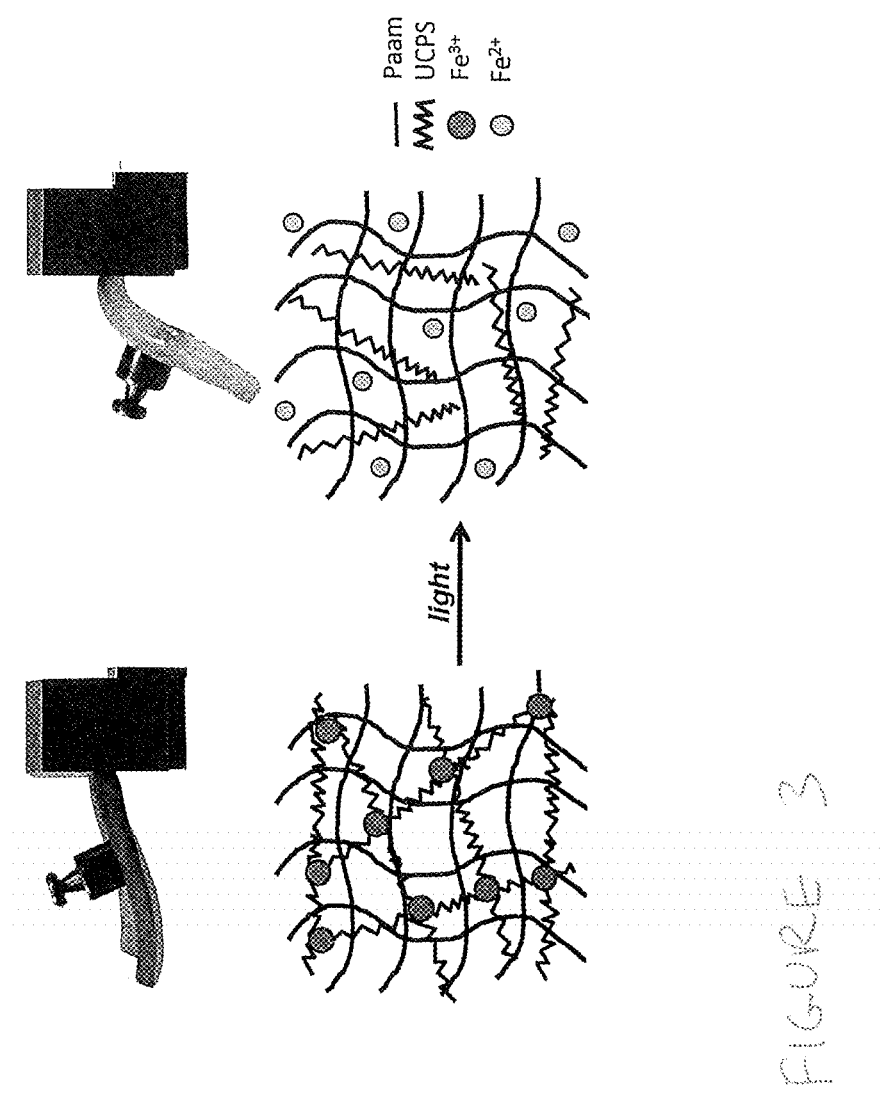
FIG. 3 shows photo-responsive Fe(III)-Paam-UCPS hydrogels in an embodiment of the invention.

The nucleic and amino acid sequences listed in the accompanying sequence listing are shown using standard letter abbreviations for nucleotide bases, and three letter code of amino acids, as defined in 37 C.F.R. § 1.822. Only one strand of each nucleic acid sequence may be shown, but the complementary strand is understood as included by any reference to the displayed strand. In the accompanying sequence listing:
SEQ ID NO: 1 shows the amino acid sequence of GGGRGDS.

DETAILED DESCRIPTION

In General:

The embodiments herein described are not intended to be exhaustive or to limit the invention to the precise forms disclosed. They are chosen and described to explain the principles of the invention and the application of the method to practical uses so that others skilled in the art may practice the invention As used in the specification and the appended claims, the singular forms "a," "an" and "the" include plural referents unless the context clearly dictates otherwise. Thus, for example, "a cell" may refer to a population of cells or reference to "a portion" may include both reference to a single portion and reference to a plurality of portions. Likewise, the use of a plural noun is to be construed as including the singular thereof, unless the context clearly dictates otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Ranges can be expressed herein as from "about" one particular value, and/or to "about" another particular value. When values are expressed as approximations, by use of the antecedent "about", it will be understood that the particular value forms another embodiment.

The use of the word "or" in this description is used conjunctively to mean one of the series, or any combination thereof, unless the context clearly dictates otherwise.

All publications and documents cited herein are incorporated to the extent permitted by law. In case of any conflict, this disclosure prevails. The citation of any document is not to be construed as an admission that it is prior art with respect to the present disclosure.

Unless otherwise noted, technical terms are used according to conventional usage. Definitions of common terms in molecular biology may be found in Benjamin Lewin, Genes V., published by Oxford University Press, 1994 (ISBN 0-19-854287-9); Kendre et al. (eds.), The Encyclopedia of Molecular Biology, published by Blackwell Science Ltd., 1994 (ISBN 0-632-2182-9); and Robert A. Meyers (ed.), Molecular Biology and Biotechnology: a Comprehensive Desk Reference, published by VCH Publishers, Inc. 1995 (ISBN 1-56081-569-8).

Abbreviations:

UCPS, uronate-containing polysaccharide; APS, ammonium persulfate, TEMED, tetramethylethylenediamine; MBA, methylene bisacrylamide; Pec, pectate; Hya, hyaluronate; Paam, polyacrylamide; LED, light emitting diode; EDTA, ethylenediaminetetraacetate; SEM scanning electron microscopy; ATR-FTIR, attenuated reflectance Fourier transformed infra-red spectroscopy; Aam, acrylamide, Alg, Alginate; ECM, extracellular matrix, sGAG, sulfated glycosaminoglycan; MES, 2-(N-morpholino)ethanesulfonic acid, PBS, phosphate buffer saline; EDC, 1-Ethyl-3-(3-dimethylaminopropyl)carbodiimide; NHS, N-Hydroxysuccinimide.

EXAMPLES

These examples are not intended to be limiting. For example, other metallic cations may be used. Various combinations of uronate containing polysaccharides can be employed without departing from the confines of the invention. The variations possible will be apparent from the disclosure herein and knowledge of one with ordinary skill in the art.

Example 1

Previously, mixed Paam-polysaccharide materials have been reported and are described as highly stretchable[12,13]

metal-ion responsive,[14] and good flocculants.[15] These materials were shown to be biocompatible and non-cytotoxic, with proven applications in drug delivery systems,[16] and as materials for tissue engineering.[17,18] Our approach is to introduce uronate-containing polysaccharides (UCPS) into polyacrylamide gels, to pro-duce mixed hydrogel networks. We used three different UCPS: alginate (Alg), pectate (Pec), and hyaluronate (Hya). These natural polysaccharides present carboxylate groups in their structure (FIG. 1). The interaction of carboxylate-bearing substrates with transition metals such as iron has been used before to create materials that respond to different stimuli to undergo structural and mechanical changes.[19-22, 23] Polyuronates alginate and pectate have been described to form photo-responsive hydrogels in the presence of Fe(III), where illumination with UV and visible light can induce changes in the physical state of the gel by triggering the reduction of the metal and the decarboxylation of the polysaccharide (FIG. 2).[22,24,25] In this work, we present for the first time Fe(III)-hyaluronate as a photo-responsive system, showing a similar behavior to Alg and Pec. The photo chemical manipulation of these systems allows for mechanical changes in the Paam-based gels upon visible light irradiation (FIG. 3). Furthermore, changes in the distribution of the polysaccharide carboxylate groups create a different dynamic in the coordination with metals.

Figure 4:
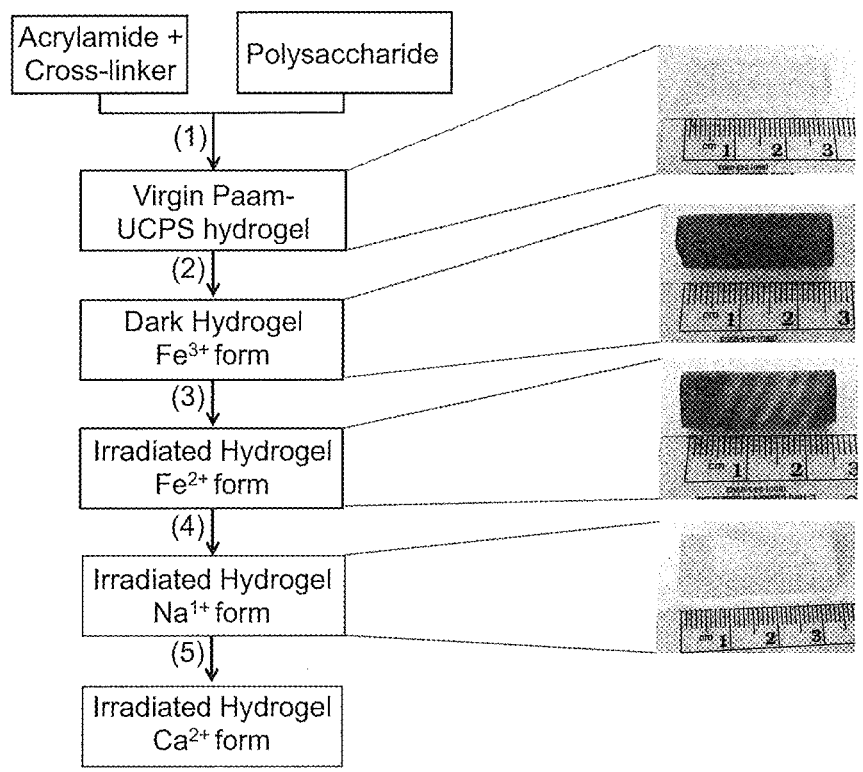
FIG. 4 shows diagram describing the steps involved in the photochemical manipulation of UCPS-Paam hydrogels in accordance with an embodiment of the invention.

The mixed gels were easily prepared by incorporating the UCPS into the Paam solution before initiating the polymerization (FIG. 4). In this reaction, the acrylamide polymerization is initiated not only by the APS/TEMED system but also by alkoxy radicals formed on the polysaccharide chain.[26,27] Both the grafting reaction and the added MBA contribute to covalent cross-linking of the material, while the carboxylates in the polysaccharide offer the opportunity to create non-covalent dynamic interactions with metals.[14]

FIG. 3 shows photo-responsive Fe(III)-Paam-UCPS hydrogels. The changes in mechanical properties can be easily illustrated by placing a 1 g weight on hydrogel film before and after irradiation under 405 nm light (145 mW/cm$^2$). The dimensions of the original film were 1.5 cm×2.3 cm×0.3 cm.

Figure 5:
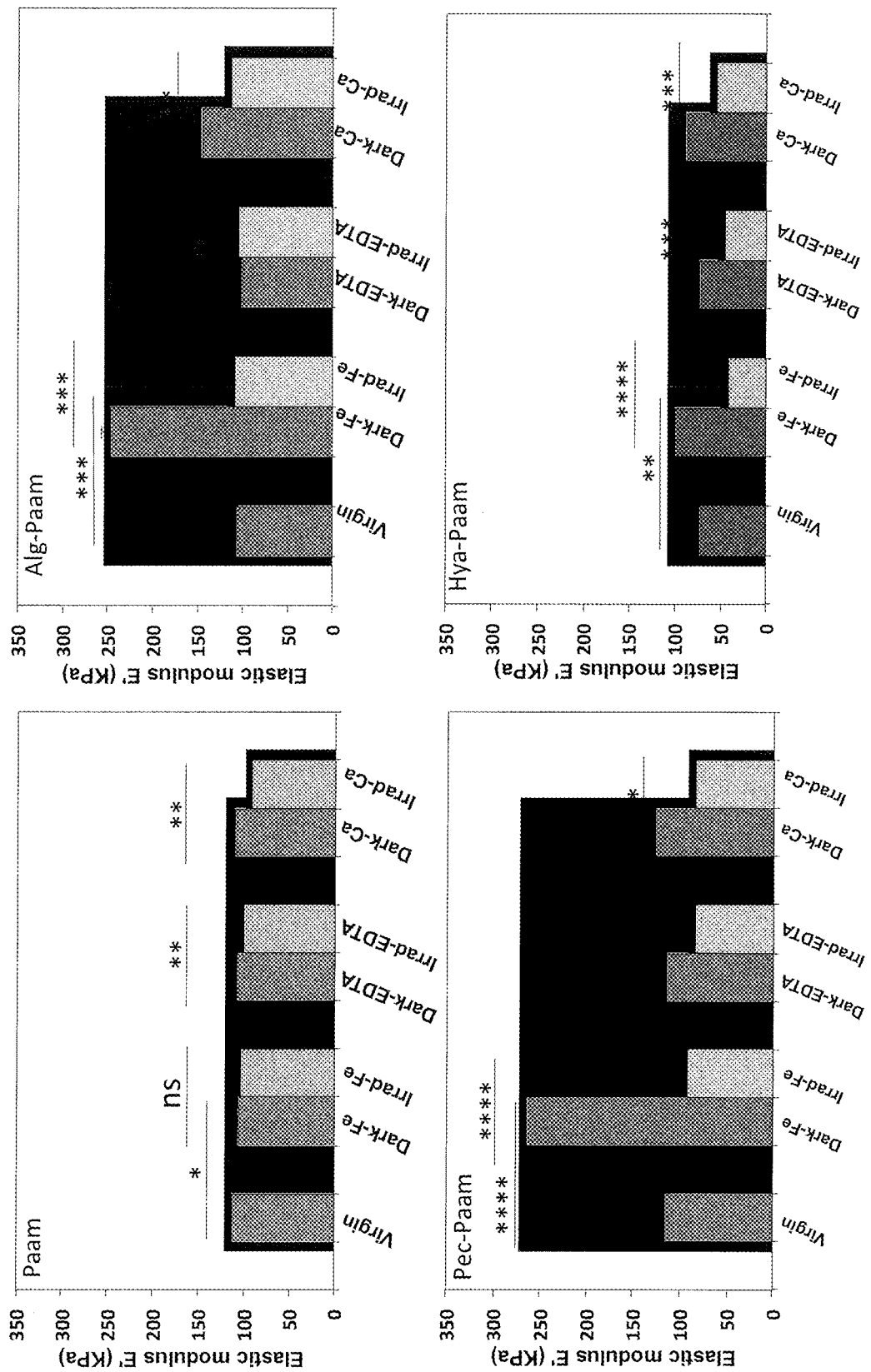
FIG. 5 shows the difference in elastic modulus for the dark vs. irradiated samples for an embodiment of the invention.

The synthesized Paam-UCPS hydrogels (virgin) were immersed in an $Fe^{3+}$ solution to create a photo-responsive material. Next, the gels were irradiated under 405 nm light for 3 h at 145 mW/cm$^2$ (Irrad-Fe) to induce irreversible mechanical and structural changes (FIGS. 3 and 5). The irradiated gels were then treated with a chelating solution to remove any Fe from the material (Irrad-EDTA). Finally, the gels were soaked in a calcium solution to induce ionic cross-linking of the polysaccharide (Irrad-Ca). All steps of the process were also performed on non-irradiated (Dark) control samples. The modification process is illustrated in FIG. 4 along with images of a sample at different stages of the process.

FIG. 5 shows evolution of the elastic moduli of the different Paam-UCPS gels at the different stages of the treatment. Irradiations were performed under 405 nm LED light (145 mW/cm$^2$) for 1800 sec. The values are expressed as the mean of N≥3 measurements and the error bar is the SD. *$P<0.05$, $P<0.01$, *$P<0.001$, ****$P<0.0001$, ns=$P≥0.05$.

Figure 6:
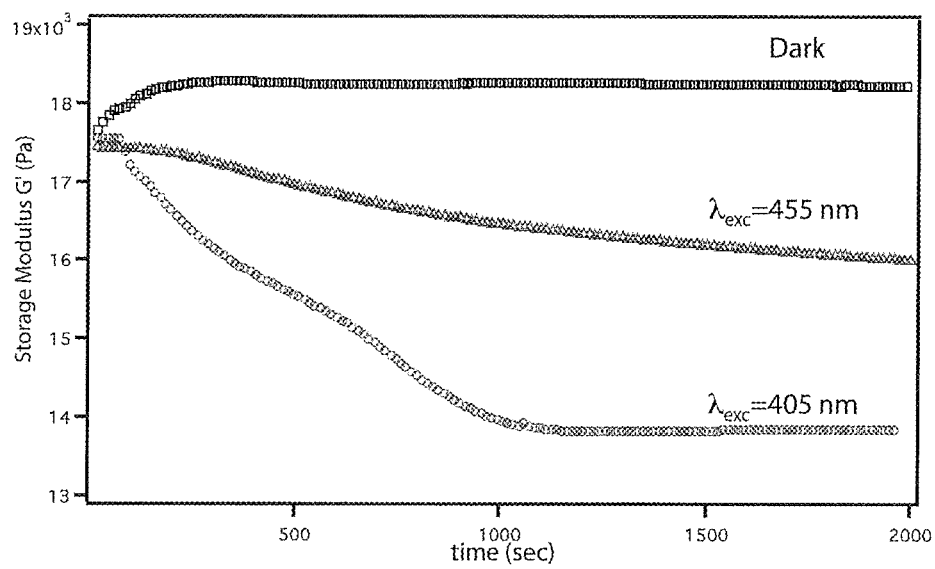
FIG. 6 shows the evolution on the storage modulus of a Pec-Paam sample upon irradiation with LED light for one embodiment of the invention.
Figure 7:
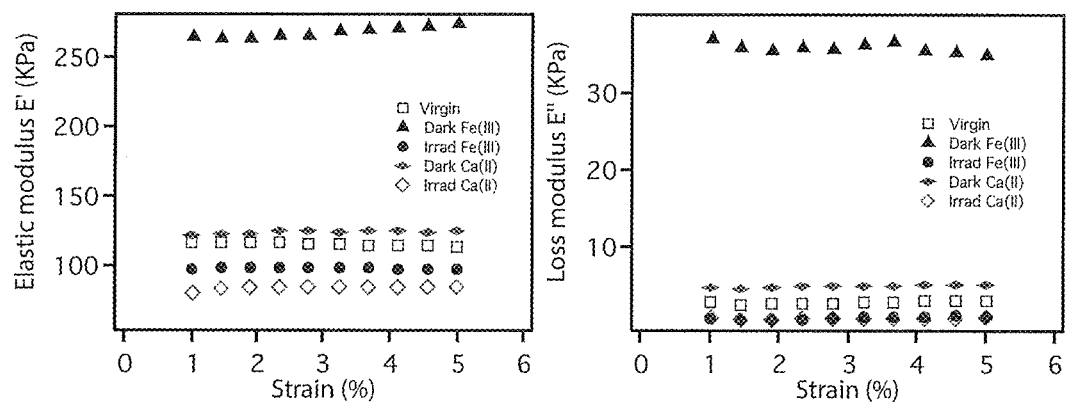
FIG. 7 shows elastic and loss modulus measurements for a Paam-Pec sample upon coordination with metals before and after irradiation for an embodiment of the invention.

The introduction of the different polysaccharides yielded materials with equal or lower elastic moduli (E') than the observed for Paam alone. (Tables 1 and 2). The trend for the elastic moduli in the series was Pec-Paam≥Paam>Alg-Paam>Hya-Paam. This trend is consistent with that expected by comparing the structure of the three polysaccharides. Pectate is a homopolymer, while alginate is a block copolymer with flexible and rigid sections both having carboxylate groups on each sugar unit. Hyauronate is an alternating polymer, were the uronic acid group is present only in every other unit (FIG. 1). By soaking these hydrogels in a solution containing $Fe^{3+}$, the uronic carboxylates on the polysaccharides can co-ordinate with the transition metal, creating new cross-links in the material and increasing its elastic modulus in all cases (Table 1). Pure Paam, however, did not show any relevant change on its elasticity, and this is attributed to the lack of Fe-coordinating groups. Iron-containing gels are photoactive due to the photo-chemistry of the $Fe^{3+}$-carboxylate moiety (FIG. 2). We explored the photo-response of these materials under 405 nm and 455 nm LED light, and both showed changes in mechanical properties. All results are reported after 405 nm light irradiation, since it produced faster changes (FIG. 6). When irradiating the hybrid $Fe^{3+}$-UCPS-Paam materials, a change in color was accompanied by a drop in the elastic modulus; which is consistent with the reduction of the iron and the change in the coordination interaction (FIG. 3). The drop in elasticity was as high as 65.7% for Pec-Paam, 59.0% for Hya-Paam, and 55.9% for Alg-Paam, and only 2.6% for Paam (FIG. 5). The loss moduli (E") also showed a drop upon irradiation, indicating a lower capacity for viscous dissipation of the energy, as the coordination interaction was lost upon irradiation (FIG. 7).

Figure 8:
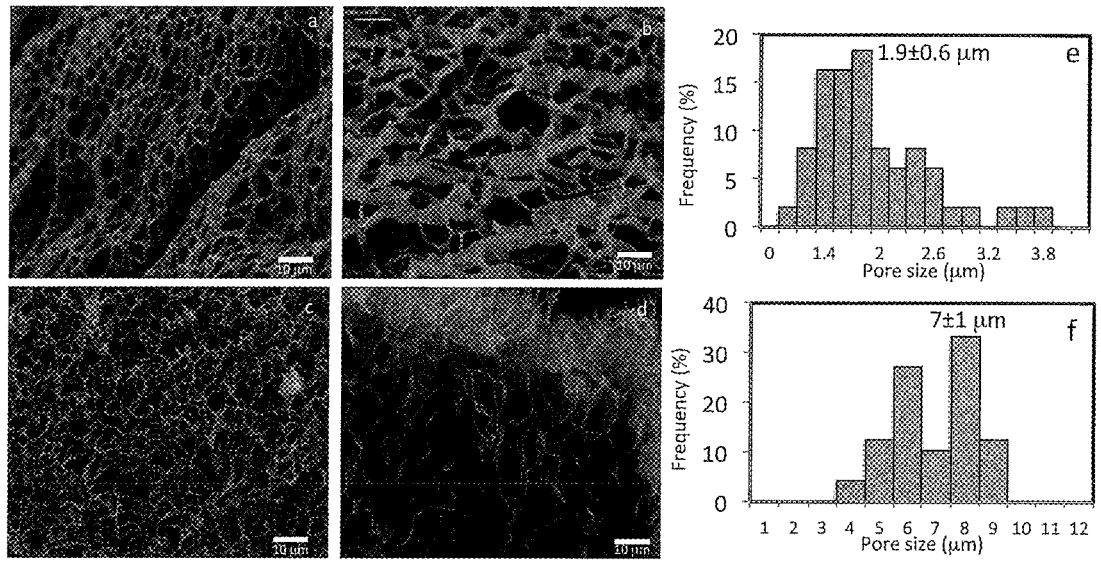
FIG. 8 shows SEM micrographs showing the pore morphology of a Fe(III)-Alg-Paam gel at the surface of the film a) before irradiation, b) after 1 h irradiation; and at the interior of the freeze-fractured gel: c) before irradiation, d) after 1 h irradiation. The histograms on the right show the average size distribution for the internal pores in the e) dark and f) irradiated materials for an embodiment of the invention.
Figure 9:
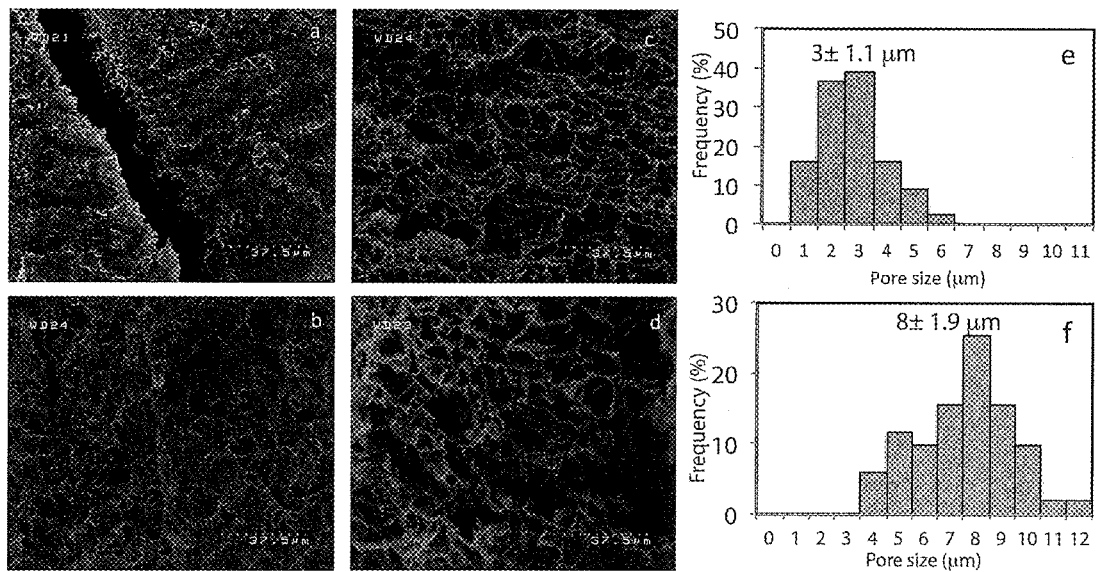
FIG. 9 shows SEM micrographs showing the pore morphology of a Fe(III)-Pec-Paam gel at the surface of the film a) before irradiation, b) after 1 h irradiation; and at the interior of the freeze-fractured gel: c) before irradiation, d) after 1 h irradiation. The histograms on the right show the average size distribution for the internal pores in the e) dark and f) irradiated materials for an embodiment of the invention.

Examination of the microstructure of by scanning electron microscopy (SEM) showed important changes in surface texture and pore size after light irradiation. Initially, the virgin hydrogels showed a non-porous surface, and a porous interior. Upon irradiation, the surface of the gels became more porous, and the internal structure changed, almost tripling the average pore size (FIGS. 8 and 9). Following this approach, we were able to create discrete patterns on these materials just by using a photo-mask during the irradiation process (FIG. 10).

Figure 10:
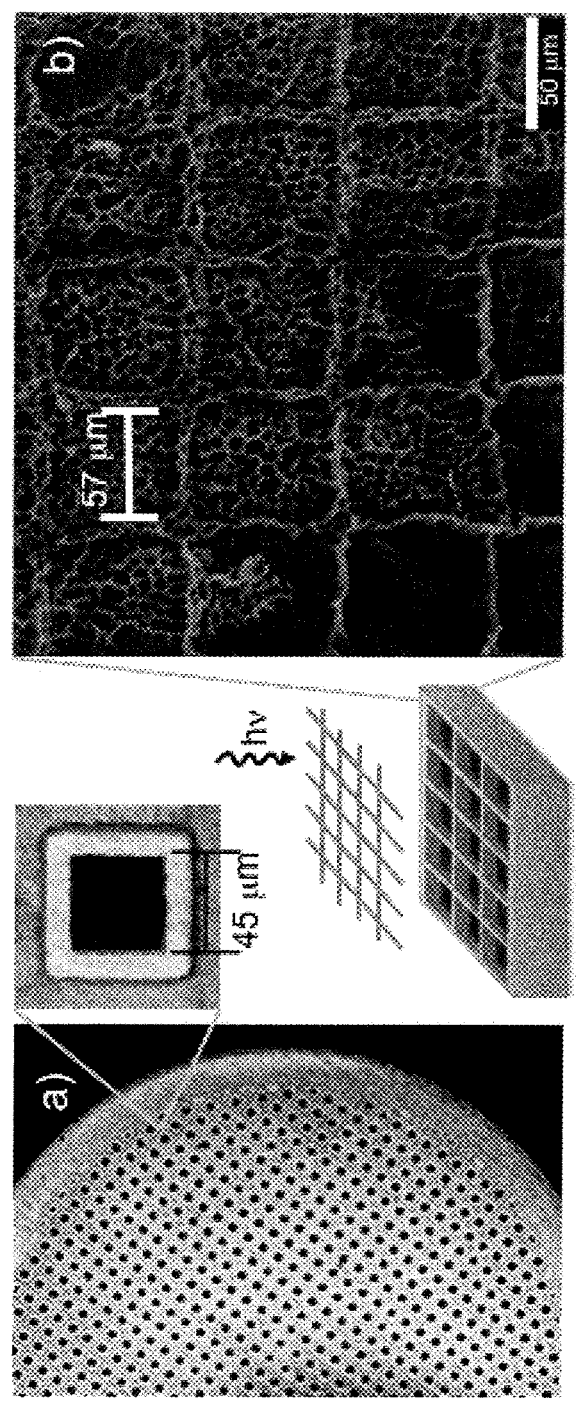
FIG. 10 shows photo-patterning of a Fe(III)-Pec-Paam hydrogel in accordance with an embodiment of the invention.

FIG. 10 shows photo-patterning of a Fe(III)-Pec-Paam hydrogel. a) Optical micrograph of the copper grid used as the photo mask, b) SEM micrograph of the photo-patterned hydrogel.

Although the dimensions of the pattern do not match those in the original grid, this can be attributed to the overall shrinking of the sample during the preparation for SEM, which results in the change of the aspect ratio of the pattern. Nevertheless, these results show that facile manipulation of light as a stimulus can give us remarkable spatial control of the material at the micron-scale.

Once irradiated, the Fe was removed from the samples using EDTA. The difference in elastic modulus for the dark vs. irradiated samples is dampened, but still observable (FIG. 5). When the samples were immersed in a calcium solution, the ionic cross-linking was restored, and an increase in elastic moduli in all the polysaccharide-containing samples was observed. The Ca-hydrogels presented lower moduli than those measured for the Fe-hydrogels, as reported before.[14] When comparing the moduli for the Ca-containing samples—dark control vs. irradiated—we see differences as high as 38.7% for Hya-Paam, 33.6% for Pec-Paam, 22.6% for Alg-Paam, and 16% for Paam (Table 2 and FIG. 2). Interestingly enough, the difference in elastic moduli is accentuated in the presence of $Ca^{2+}$ (FIG. 5). Here, the lower elastic modulus of the irradiated samples can be attributed to the loss of carboxylate functional groups in the irradiated areas, changing the ability of the material to coordinate metals. These results show important differences in the tunability of the mechanical properties of these materials, and most importantly, a trend for the photo-responsiveness in these systems. The aforementioned trend was also observed when the shear modulus of these materials was studied at the different stages of the process (Table 2 and FIG. 11). In this case, the drop in storage modulus for the $Ca^{2+}$-containing samples was 50.0% for Hya-Paam, 54.9% for Pec-Paam, 40% for Alg-Paam, and 12.2% for pure Paam. The changes on the Paam control, although statistically significant, were not as important as the ones observed for the gels in which the UCPS were present. However, these results suggest that the treatment of the gel with Fe(III) and light gave rise to chemical changes in the material, even if the polysaccharide was not present. The photo-induced depolymerization of linear polyacrylamide irradiated under sunlight in the presence of Fe(III) has been observed.[28]

We used ATR-FTIR spectroscopy to explore the changes in chemical composition at the surface of the gels. Although the signals of the Paam (major component) dominate the spectrum of these materials (FIG. 12), small but significant changes in the spectrum of the irradiated samples confirm that the composition of the materials has changed. In the case of alginate, for example, the carbonyl stretching for the protonated polysaccharide ($v=1740$ cm-1) can be observed as a small band in the spectrum of the mixed hydrogel (FIG. 13). The relative intensity of this signal decreases significantly upon the photo-chemical treatment of the sample, which agrees with the decarboxylation of the polysaccharide.[25] Similarly, the broad signal around 1029 cm-1, assigned to the C—O stretching with contributions of —C—C—O— and —C—C— vibrations of the polysaccharide,[29,30] showed a much lower intensity for the irradiated material.

This could be an indicative of a degradation of the glycosidic linkages and lower content of the polysaccharide in-side the hydrogel. Since the photo excitation of these materials led to loss of carboxylate groups that can coordinate metal ions, we expect lower concentrations of these species in areas of the greatest light exposure. This allows for creating gradients of concentration of biologically relevant metal ions, e.g. copper, zinc, and magnesium by modulating the carboxylate binding groups.

FIG. 13 shows Normalized ATR-FTIR spectra of a) Alginic acid, b) Paam, c) virgin Alg-Paam, and d) irradiated Alg-Paam. The black arrows indicate the alginate signals decreasing upon irradiation.

Figure 13:
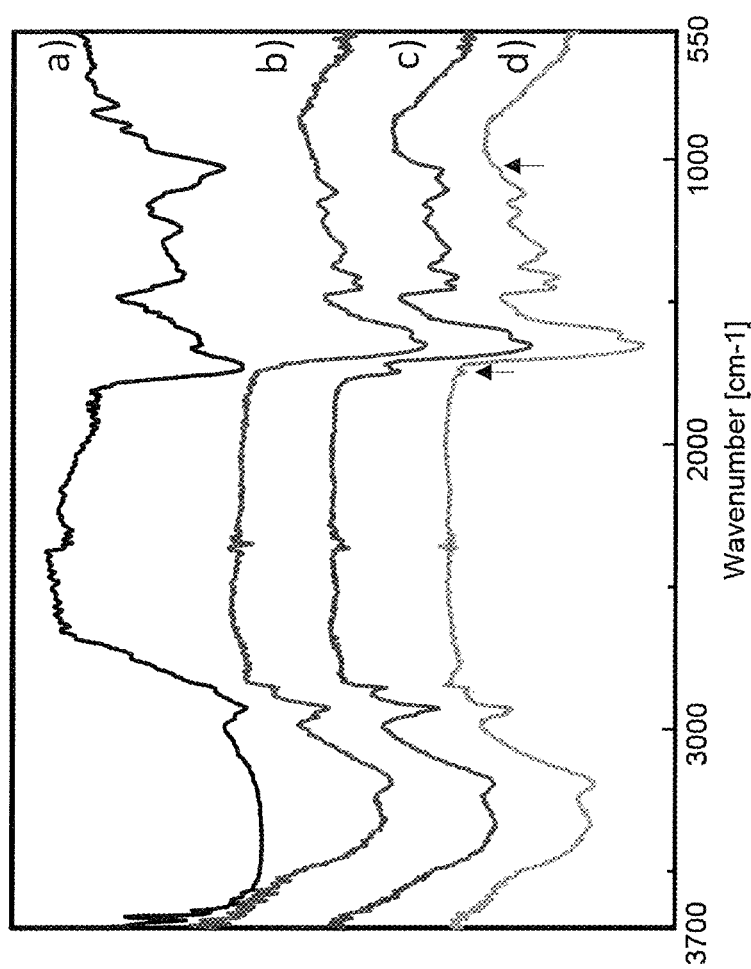
FIG. 13 shows Normalized ATR-FTIR spectra of a) Alginic acid, b) Paam, c) virgin Alg-Paam, and d) irradiated Alg-Paam for an embodiment of the invention.
Figure 14:
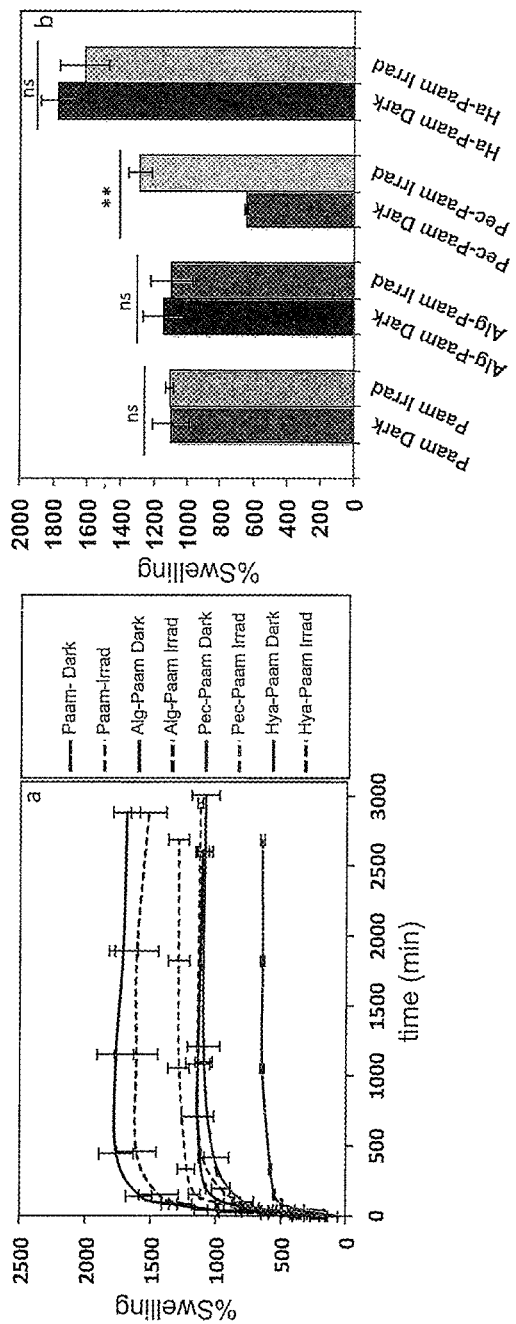
FIG. 14 shows an embodiment of the invention where a) swelling behavior of the different hydrogels in saline phosphate buffer pH=7.01 at 25° C. and b) maximum % swelling for the different hydrogel systems.

Although a photo-induced decarboxylation was observed during the irradiation process (FIG. 13)[25,31] the swelling capacity of the gels was not statistically different, except for Pec-Paam, which became as swellable as Paam or Alg-Paam after being irradiated (FIG. 14). The higher stiffness of Pec-Paam (Table 1) can contribute to the lower swelling of the material. Therefore, in this case, the photochemical treatment of the gel decreases the molecular weight of the polysaccharide, affording a softer material with a higher capacity for absorbing water in the conditions of the experiment.

Our results show how the introduction of UCPS in a synthetic, biocompatible gel such as Paam, provides the ability to coordinate photo-active metals like Fe(III), which opens the door to the creation of advanced materials with specific gradients and interfaces of mechanical properties that would exist in natural tissues. Our preliminary results indicate changes in the elastic modulus of these hydrogels in ranges that match the stiffness of human tissue.[1,5,7]

Moreover, the photochemical treatment induced measurable changes in the material microstructure, increasing the size of the pores in the gel, which has proven to have important effects when cells are growing on Paam substrates.[10] Furthermore, the photochemical patterning changed the distribution of carboxylate groups in the gels, changing the capacity for interacting with different metal ions. Once these patterns are created, the Fe(III) ions can be removed and exchanged for Ca(II), maintaining the changes induced during the irradiation.

Future work will focus on the evaluation of these materials in cell cultures for toxicity, biocompatibility, and evaluation of their performance as substrates for inducing stem cell differentiation. In addition, we plan to change the pore size of the prepared gels to further tune the dynamics of the interface between the cells and the scaffold material. The photochemical manipulation of Fe(III)-UCPS containing hydrogels shows potential as a method for designing substrates with specific mechanical properties, with potential uses in biomedicine and tissue engineering.

Materials

Low viscosity sodium alginate from brown algae (Mv 45,000 g/mol) (Lot A112) was purchased from Sigma-Aldrich and used as received. Poly-D-galacturonic acid 95%, Mw 25,000-50,000 g/mol (Lot. 81325) was purchased from Sigma-Aldrich and prepared as the sodium salt by neutralization with NaOH. This material is referred to as "pectate". Hyaluronic acid sodium salt from *Streptococcus equi*, Mw 1,500,000-1,800,000 g/mol was purchased form Sigma-Aldrich and used as received. Ferric chloride hexahydrate 98%, was purchased from Fluka and used as received, only freshly prepared solutions from this reagent were used. Acrylamide (Aam), methylene bis-acrylamide (MBA), ammonium persulfate (APS), and Tetramethylethylenediamine (TEMED) were purchased from Sigma Aldrich and used as received.

Synthesis of Paam-UCPS Hydrogels

For the synthesis of the mixed gels, we first prepared an 8% wt solution of acrylamide in deionized water, containing 0.48% wt in MBA. Then, 3% wt homogeneous solutions were prepared by dissolving the sodium salt of the polysaccharide in the Aam stock. The polymerization was performed using APS (0.2% wt) as the initiator, and TEMED (0.2% wt) as the accelerator. After incorporating the initiation system, the solutions were poured in between two slides with a 1 mm-thickness PDMS spacer and sonicated to eliminate any air bubble present in the sample. The gels were allowed to cure overnight at room temperature. Hydrogel films were removed from the molds and rinsed with DI water at least three times over a 6 h period in order to equilibrate them and eliminate any unreacted starting material. Hydrogel cylinders as the one showed in FIG. 4 were prepared by polymerization of the UCPS-Aam system using a 3 mL plastic syringe as the mold.

Photochemical Manipulation of Hydrogels

The equilibrated hydrogel films were immersed in a 0.1 M $FeCl_3$ solution for 2 h. All samples containing iron were kept in the dark until the irradiation experiments were performed.

The iron-containing samples were rinsed and maintained in DI water for the duration of the irradiation experiments. Samples were irradiated for 180 min by using a 405 nm LED lamp (Thorlabs). The intensity of light at the surface of the gels (irradiance) was 145 $mW/cm^2$, as measured with a S121C photodiode power sensor (Thorlabs). After irradiation, the specimens were demetallated by immersing them in a 0.025 M EDTA solution, and placing samples solutions on an orbital shaker. The extracting medium was replaced three times over 24 h period, and the procedure was repeated with DI water. When needed, samples were immersed in a 0.1 M $CaCl_2$ solution for 6 h and then rinsed with DI water before measuring the mechanical properties.

For the photochemical patterning, the iron form of the gel was irradiated for 60 min under 405 nm LED light (29 mW/cm$^2$) using a 300-mesh TEM grid as a photomask. The samples were carefully rinsed with DI water and freeze-dried immediately after.

Mechanical Properties Measurements

Sections of the prepared hydrogel films were punch-cut and equilibrated in aqueous solutions before their analysis. The study of the mechanical properties was performed in a TA Instruments HR2-Discovery hybrid rheometer equipped a peltier plate with the parallel plates geometry. All measurements were conducted at 25.0° C. and the specimens were kept immersed in water during the analysis. Elastic moduli where measured from compression experiments. The axial force was kept at 1.0 N and the sample was compressed from 1.0-5.0% axial strain at 1 Hz.

Storage moduli were measured from dynamic shear experiments. Samples were sheared keeping the frequency at 1 Hz and sweeping the strain from 1-100%. The reported moduli correspond to strains below 50%, where the response was linear.

Scanning Electron Microscopy.

Samples were freeze-dried and sputter coated with Au/Pd. SEM images were collected on a Hitachi S2700 scanning electron microscope.

FTIR Analysis

Samples were soaked for 1 hour in a 0.01 M HCl solution in order to protonate the uronate units and avoid the overlapping of the carboxylate signal with the amide bands form Paam. Next, the protonated gels were rinsed with DI water and freeze dried. The xerogels were placed on the ATR crystal. Infrared spectra were collected in a Jasco FTIR-4000 equipped with a single reflection ATR accessory.

Swelling Experiments

The hydrogel samples were punch-cut to get 8 mm-diameter discs. Specimens were oven-dried at 40° C. for 24 h and then stored in a desiccator. The samples were swollen in PBS buffer, pH=7.04 at 25° C. Gravimetric analysis was performed to determine the amount of swelling.

Statistical Analysis

Mechanical properties and swelling analyses were, at minimum, triplicated, using in all cases samples from different areas of the film, and the results are reported ±SD. The Student's t-test was used to compare the results from the mechanical testing. P values<0.05 were considered significant. N values were ≥3.

FIG. 1 Chemical structures of the different uronate containing polysaccharides (UCPS) used to create hybrid polyacrylamide gels.

FIG. 2A Photo-induced degradation of Fe(III)-UCPS to induce of loss of the coordination crosslinking and degradation of the polysaccharide.

FIG. 4. Diagram describing the steps involved in the photochemical manipulation of UCPS-Paam hydrogels. (1) APS, TEMED, RT (2) 0.1 M FeCl$_3$ (3) λ=405 nm, 120 min at 145 mW/cm$^2$ (4) 0.025M EDTA (5) 0.1 M CaCl$_2$. The images on the right show an example of a Alg-Paam hydrogel in which a line pattern has been imprinted.

FIG. 6 Evolution on the storage modulus of a Pec-Paam sample upon irradiation with LED light.

FIG. 7 Elastic and loss modulus measurements for a Paam-Pec sample upon coordination with metals before and after irradiation.

FIG. 8 SEM micrographs showing the pore morphology of a Fe(III)-Alg-Paam gel at the surface of the film a) before irradiation, b) after 1 h irradiation; and at the interior of the freeze-fractured gel: c) before irradiation, d) after 1 h irradiation. The histograms on the right show the average size distribution for the internal pores in the e) dark and f) irradiated materials.

FIG. 9 SEM micrographs showing the pore morphology of a Fe(III)-Pec-Paam gel at the surface of the film a) before irradiation, b) after 1 h irradiation; and at the interior of the freeze-fractured gel: c) before irradiation, d) after 1 h irradiation. The histograms on the right show the average size distribution for the internal pores in the e) dark and f) irradiated materials.

Figure 11:
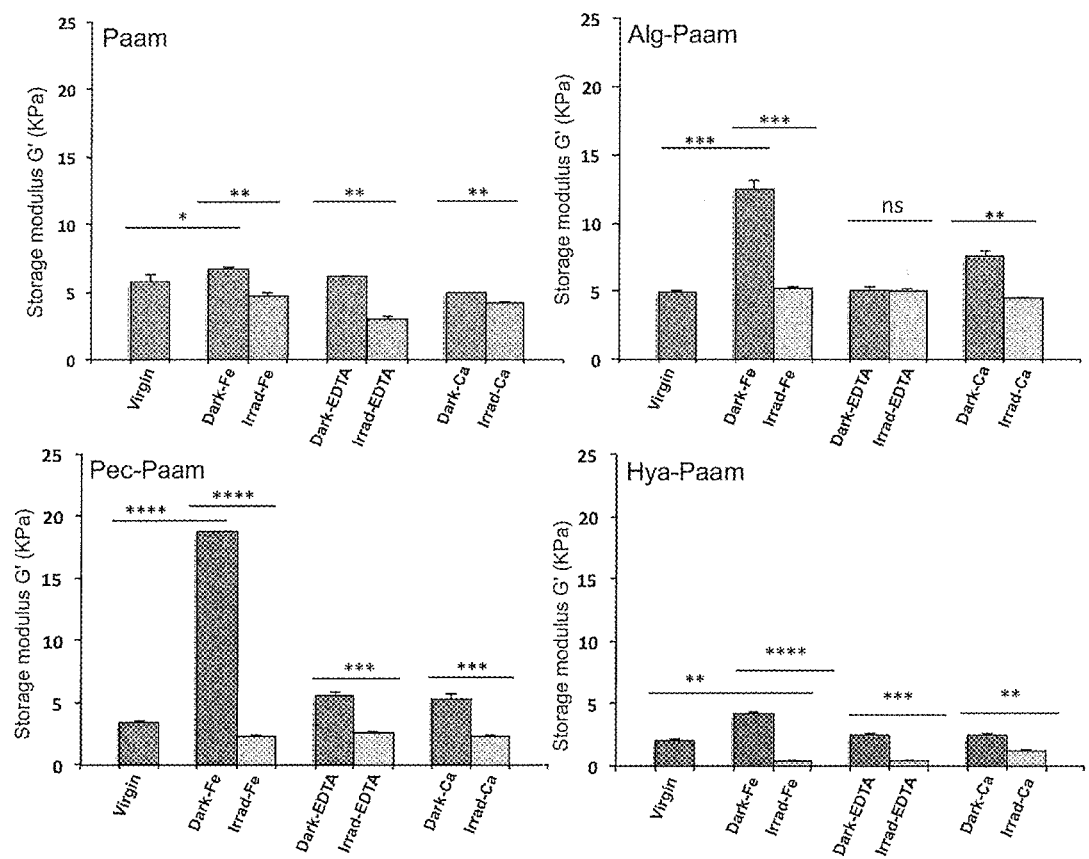
FIG. 11 Storage moduli measured for the different hydrogel systems at different steps of the process for an embodiment of the invention.

FIG. 11 Storage moduli measured for the different hydrogel systems at different steps of the process. Irradiations were performed under 405 nm LED light (145 mW/cm$^2$) for 1800 sec. The values are expressed as the mean of N≥3 measurements and the error bar is the SD. *P<0.05, P<0.01, *P<0.001, ****P<0.0001, ns=P≥0.05

Figure 12:
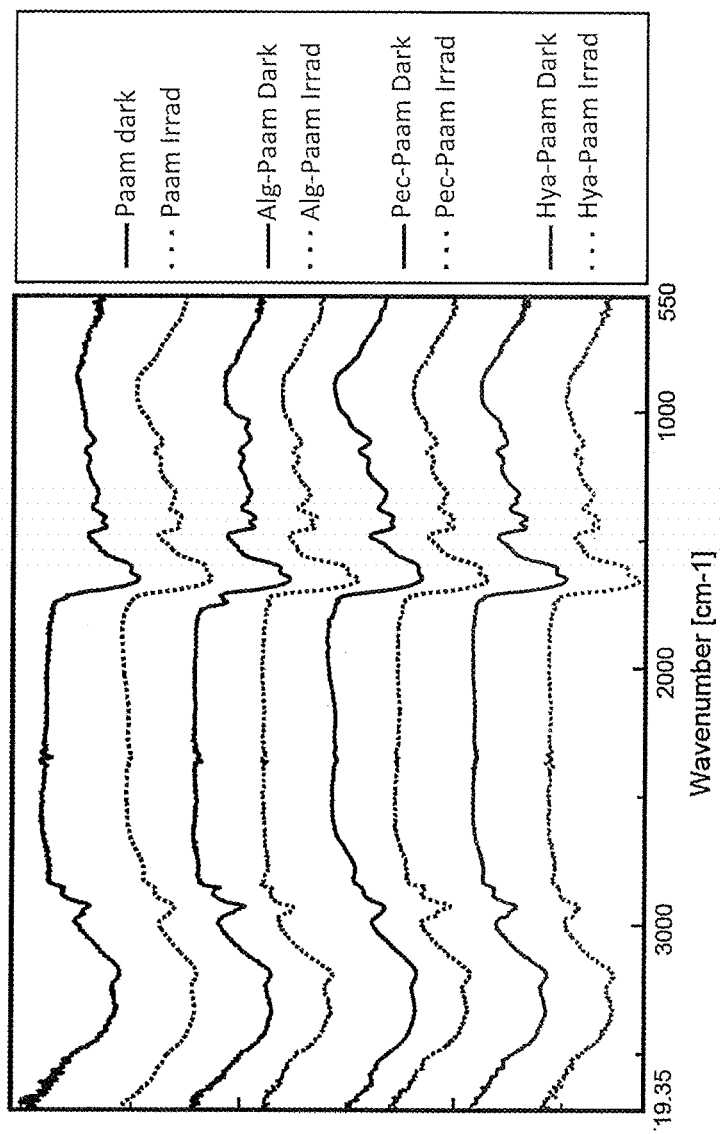
FIG. 12 shows ATR-FTIR of the studied hydrogels before the light treatment (dark) and after irradiation and removal of the iron (irrad) for an embodiment of the invention.

FIG. 12 ATR-FTIR of the studied hydrogels before the light treatment (dark) and after irradiation and removal of the iron (irrad): Samples were protonated before lyophilization.

FIG. 14 a) Swelling behavior of the different hydrogels in saline phosphate buffer pH=7.01 at 25° C. b) Maximum % swelling for the different hydrogel systems.

REFERENCES FOR EXAMPLE 1

(1) Higuchi, A.; Ling, Q.-D.; Chang, Y.; Hsu, S.-T.; Umezawa, A. Physical Cues of Biomaterials Guide Stem Cell Differentiation Fate. Chem. Rev. 2013, 113, 3297-3328.

(2) Lee, J.; Abdeen, A. A.; Zhang, D.; Kilian, K. A. Directing Stem Cell Fate on Hydrogel Substrates by Controlling Cell Geometry, Matrix Mechanics and Adhesion Ligand Composition. Biomaterials 2013, 34, 8140-8148.

(3) Tse, J. R.; Engler, A. J. Stiffness Gradients Mimicking In Vivo Tissue Variation Regulate Mesenchymal Stem Cell Fate. PLoS ONE 2011, 6, e15978.

(4) Wang, H.; Leinwand, L. A.; Anseth, K. S. Cardiac Valve Cells and Their Microenvironment-insights from in Vitro Studies. Nat Rev Cardiol 2014, 11, 715-727.

(5) Vincent, L. G.; Choi, Y. S.; Alonso-Latorre, B.; del Álamo, J. C.; Engler, A. J. Mesenchymal Stem Cell Durotaxis Depends on Substrate Stiffness Gradient Strength. Biotechnol. J. 2013, 8, 472-484.

(6) Tokuda, E. Y.; Leight, J. L.; Anseth, K. S. Modulation of Matrix Elasticity with PEG Hydrogels to Study Melanoma Drug Responsiveness. Biomaterials 2014, 35, 4310-4318.

(7) Engler, A. J.; Sen, S.; Sweeney, H. L.; Discher, D. E. Matrix Elasticity Directs Stem Cell Lineage Specification. Cell 2006, 126, 677-689.

(8) Wang, P.-Y.; Tsai, W.-B.; Voelcker, N. H. Screening of Rat Mesenchymal Stem Cell Behaviour on Polydimethylsiloxane Stiffness Gradients. Acta Biomater. 2012, 8, 519-530.

(9) Tse, J. R.; Engler, A. J. Preparation of Hydrogel Substrates with Tunable Mechanical Properties. In Current Protocols in Cell Biology; Bonifacino, J. S.; Dasso, M.; Harford, J. B.; Lippincott-Schwartz, J.; Yamada, K. M., Eds.; John Wiley & Sons, Inc.: Hoboken, N.J., USA, 2010.

(10) Trappmann, B.; Gautrot, J. E.; Connelly, J. T.; Strange, D. G. T.; Li, Y.; Oyen, M. L.; Cohen Stuart, M. A.; Boehm, H.; Li, B.; Vogel, V.; et al. Extracellular-Matrix Tethering Regulates Stem-Cell Fate. Nat. Mater. 2012, 11, 642-649.

(11) Sunyer, R.; Jin, A. J.; Nossal, R.; Sackett, D. L. Fabri-cation of Hydrogels with Steep Stiffness Gradients for Studying Cell Mechanical Response. PLoS ONE 2012, 7, e46107.
(12) Sun, J.-Y.; Zhao, X.; Illeperuma, W. R. K.; Chaudhuri, O.; Oh, K. H.; Mooney, D. J.; Vlassak, J. J.; Suo, Z. Highly Stretchable and Tough Hydrogels. Nature 2012, 489, 133-136.
(13) Hossein Omidian, J. G. R. Elastic, Superporous Hydrogel Hybrids of Polyacrylamide and Sodium Alginate. Mac-romol. Biosci. 2006, 6, 703-710.
(14) Yang, C. H.; Wang, M. X.; Haider, H.; Yang, J. H.; Sun, J.-Y.; Chen, Y. M.; Zhou, J.; Suo, Z. Strengthening Alginate/polyacrylamide Hydrogels Using Various Multivalent Cations. ACS Appl. Mater. Interfaces 2013, 5, 10418-10422.
(15) Tripathy, T.; Pandey, S. R.; Karmakar, N. C.; Bhagat, R. P.; Singh, R. P. Novel Flocculating Agent Based on Sodium Alginate and Acrylamide. Eur. Polym. J. 1999, 35, 2057-2072.
(16) Tripathi, R.; Mishra, B. "Development and Evaluation of Sodium Alginate-Polyacrylamide Graft-Co-Polymer-Based Stomach Targeted Hydrogels of Famotidine." AAPS Pharm Sci Tech 2012, 13, 1091-1102.
(17) Darnell, M. C.; Sun, J.-Y.; Mehta, M.; Johnson, C.; Arany, P. R.; Suo, Z.; Mooney, D. J. Performance and Biocompatibility of Extremely Tough Alginate/polyacrylamide Hydro-gels. Biomaterials 2013, 34, 8042-8048.
(18) Guo, P.; Yuan, Y.; Chi, F. Biomimetic Alginate/polyacrylamide Porous Scaffold Supports Human Mesenchymal Stem Cell Proliferation and Chondrogenesis. Mater. Sci. Eng. C 2014, 42, 622-628.
(19) He, S.; Ren, B.; Liu, X.; Tong, Z. Reversible Electrogelation in Poly(acrylic Acid) Aqueous Solutions Triggered by Redox Reactions of Counterions. Macromol. Chem. Phys. 2010, 211, 2497-2502.
(20) Peng, F.; Li, G.; Liu, X.; Wu, S.; Tong, Z. Redox-Responsive Gel-Sol/Sol-Gel Transition in Poly(acrylic Acid) Aqueous Solution Containing Fe(III) Ions Switched by Light. J. Am. Chem. Soc. 2008, 130, 16166-16167.
(21) Auletta, J. T.; LeDonne, G. J.; Gronborg, K. C.; Ladd, C. D.; Liu, H.; Clark, W. W.; Meyer, T. Y. Stimuli-Responsive Iron-Cross-Linked Hydrogels That Undergo Redox-Driven Switching between Hard and Soft States. Macromolecules 2015, 48, 1736-1747.
(22) Narayanan, R. P.; Melman, G.; Letourneau, N. J.; Mendelson, N. L.; Melman, A. Photodegradable iron(III) Cross-Linked Alginate Gels. Biomacromolecules 2012, 13, 2465-2471.
(23) Jin, Z.; Güven, G.; Bocharova, V.; Halámek, J.; Tokarev, I.; Minko, S.; Melman, A.; Mandler, D.; Katz, E. Electro-chemically Controlled Drug-Mimicking Protein Release from Iron-Alginate Thin-Films Associated with an Electrode. ACS Appt. Mater. Interfaces 2012, 4, 466-475.
(24) Bruchet, M.; Mendelson, N. L.; Melman, A. Photochemical Patterning of Ionically Cross-Linked Hydrogels. Processes 2013, 1, 153-166.
(25) Giammanco, G. E.; Sosnofsky, C. T.; Ostrowski, A. D. Light-Responsive Iron(III)-Polysaccharide Coordination Hydrogels for Controlled Delivery. ACS Appl. Mater. Interfaces 2015, 7, 3068-3076.
(26) Kulkarni, R. V.; Boppana, R.; Krishna Mohan, G.; Mu-talik, S.; Kalyane, N. V. pH-Responsive Interpenetrating Network Hydrogel Beads of Poly(acrylamide)-G-Carrageenan and Sodium Alginate for Intestinal Targeted Drug Delivery: Synthesis, in Vitro and in Vivo Evaluation. J. Colloid Interface Sci. 2012, 367, 509-517.
(27) Maia, A. M. S.; Silva, H. V. M.; Curti, P. S.; Balaban, R. C. Study of the Reaction of Grafting Acrylamide onto Xanthan Gum. Carbohydr. Polym. 2012, 90, 778-783.
(28) Woodrow, J. E.; Seiber, J. N.; Miller, G. C. Acrylamide Release Resulting from Sunlight Irradiation of Aqueous Polyacrylamide/Iron Mixtures. J. Agric. Food Chem. 2008, 56, 2773-2779.
(29) Leal, D.; Matsuhiro, B.; Rossi, M.; Caruso, F. FT-IR Spectra of Alginic Acid Block Fractions in Three Species of Brown Seaweeds. Carbohydr. Res. 2008, 343, 308-316.
(30) Li-Chan, E.; Chalmers, J.; Griffiths, P. Applications of Vibrational Spectroscopy in Food Science; John Wiley & Sons, 2011.
(31) Okajima, M. K.; Ie Nguyen, Q. T.; Tateyama, S.; Ma-suyama, H.; Tanaka, T.; Mitsumata, T.; Kaneko, T. Photoshrinkage in Polysaccharide Gels with Trivalent Metal Ions. Biomacromolecules 2012, 13, 4158-4163.

Example 2

Hydrogels are common and convenient substrates for tissue engineering[1] since these soft materials often provide a stable platform for cells to adhere, grow, and function.[1,2] The rich and reproducible chemistry of polymeric hydrogel materials offers a myriad of opportunities for the design and preparation of scaffolds for tissue culture with different functionalities.[1] The new challenge, however, is to be able to easily to tailor the functionality and properties of these synthetic scaffolds in order to improve the quality of the cultured tissue. This is important, since the scaffold materials need to mimic the extra cellular matrix (ECM), which is not just a passive support for the cells, but it is capable of sending both chemical and mechanical cues that ultimately control and direct the fate of the growing tissue.[3-5]

It has been shown that the mechanical properties of tissue engineering scaffolds can be used to control and direct important aspects of cell development, such as adhesion, growth, morphology, signaling, motility and survival.[3,5-7] Porosity has been described as another factor having a strong influence in the performance of the scaffolds for cell support. The pores on the ECM serve as channels for transporting nutrients and waste, and allow for the vascularization of some tissues.[8,9] In addition, porosity also affects the bulk mechanical properties of these support materials.[8] One of the needs of regenerative medicine then, is to have access to functional synthetic materials with the ability to easily control the chemical and mechanical cues (like porosity) to determine the different roles in the development of the cultured tissue.[10] Hydrogels prepared from alginate and acrylamide (AlgAam) have received attention recently due to the interesting properties that these hybrid materials present. The network created from these two elements has shown to be highly stretchable,[11,12] tough,[11, 13, 14] stimuli responsive[15-19] and biocompatible.[13,20] The high stiffness and toughness of this hybrid network brings it close to the properties of load-bearing biological tissues such as cartilage.[13,21] Most recently, our group reported that the interaction of these gels with ferric ions, renders the material reactive towards visible light exposure.[19] The photochemical process involved has been described as a photo-induce electron transfer that results in the reduction of the metal and ultimate degradation of the polysaccharide (FIG. 15).[22,23] These irreversible transformations at the molecular level manifest as changes in the macroscopic properties of the hydrogel, with changes in the pore structure and stiffness of the materials upon irradiation (FIG. 16).[19] Herein, we provide further characterization of the responsive AlgAam materials described in the published communication[19], including the effect of light irradiation on the swelling properties and transport mechanisms of this hybrid material. In addition, we use these photoresponsive materials as tissue engineering substrates, where we easily tuned the pore size and mechanical properties of the materials using light irradiation.

Figure 16:
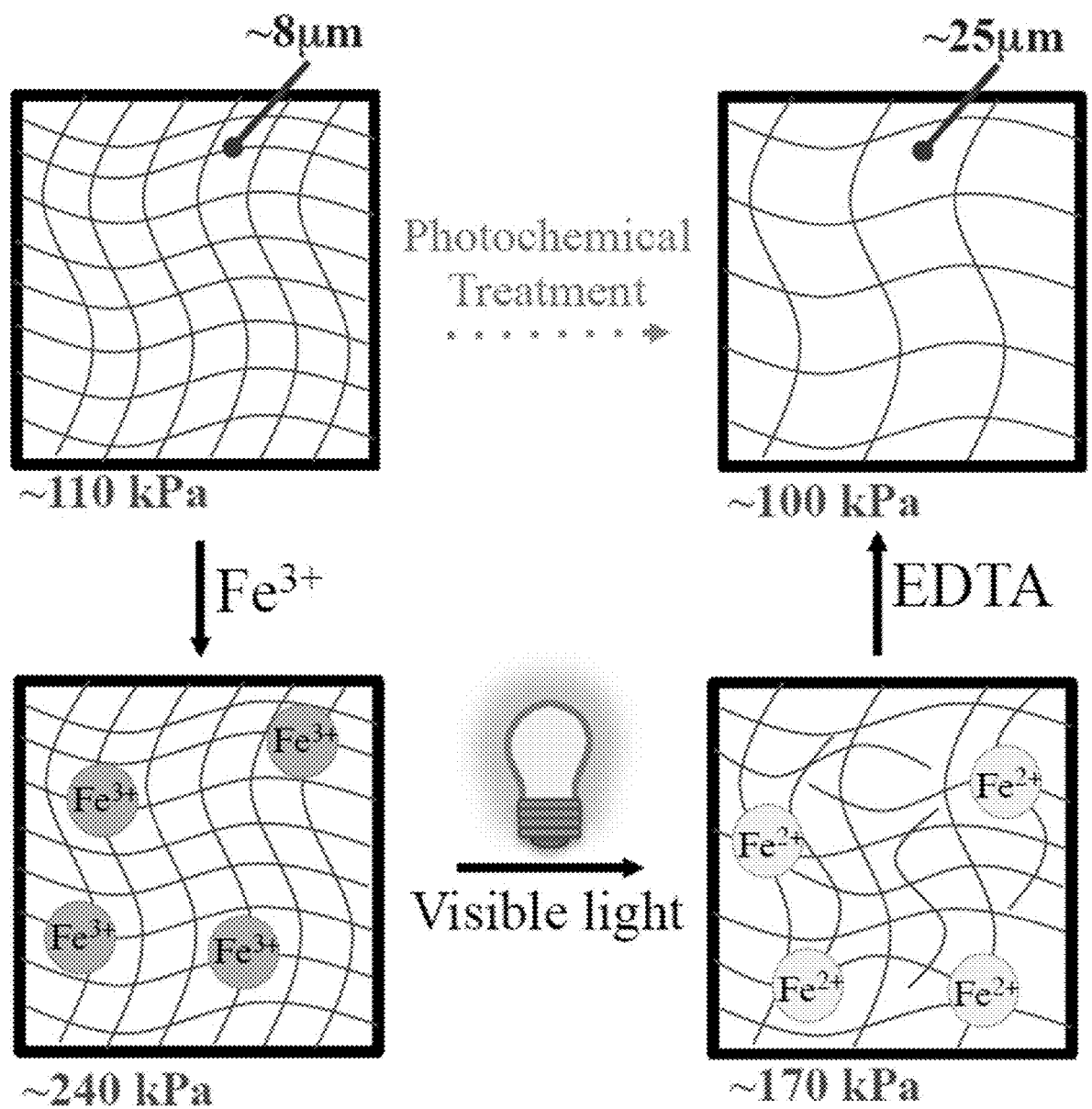
FIG. 16 shows a schematic representation of the photochemical treatment of Alg-containing hydrogels in accordance with an embodiment of the invention.
Figure 13:
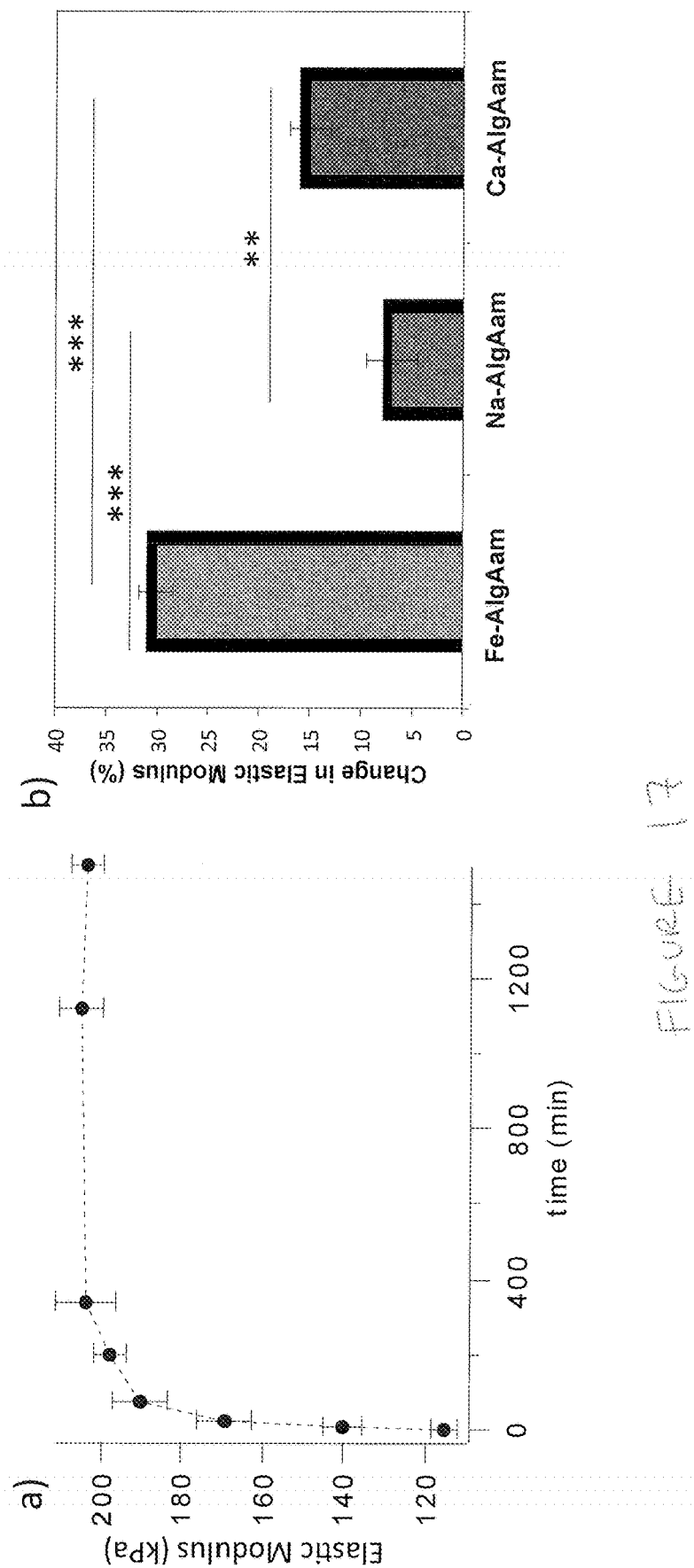

FIG. 16. Schematic representation of the photochemical treatment of Alg-containing hydrogels. The values in red represent the elastic moduli measured by dynamic compression. The values in blue represent the average pore diameter as measured by SEM.

Specifically, we explored the suitability of these gels as substrates for cartilage producing cell culture and our results show that the cells successfully underwent chondrogenesis and produced variable amounts of ECM. There was a significant increase in the production of sulfated proteoglycans when culturing cells in the AlgAam scaffold that was modified with photochemical treatment of the material, compared to those as prepared. This shows that our method of photochemical treatment of AlgAam materials was effective in tailoring the properties of the scaffold, and ultimately modulated cartilage production.

2. Materials and Methods 2.1. Materials. Low viscosity sodium alginate from brown algae (Alg) (Mv 45,000 g/mol) (Lot A112), acrylamide (Aam), methylenebisacrylamide (MBA), tetramethylethylenediamine (TEMED), sodium azide, and ethylenediaminetetraacetic acid (EDTA) disodium salt, were purchased from Sigma-Aldrich and used as received. Ferric Chloride hexahydrate was purchased from Sigma-Aldrich; only freshly prepared solutions of this reagent were used. 2-(N-morpholino) ethanesulsulfonic acid (MES) was purchased from TCI and used as received. The GGGRGDS synthetic peptide (SEQ ID NO: 1) was purchased from GenScript (Piscataway, N.J.). 1-ethyl-3-(3-dimethylaminopropyl)carbodiimide hydrochloride (EDC), N-hydroxysuccinimide (NHS), and Texas Red-labeled dextran, 70 kDa, were purchased from Thermo Fisher and used as received.

2.2. Methods 2.2.1. Hydrogel synthesis. Alginate-Paam hydrogels were prepared by radical polymerization of the acrylic monomer in the presence of the polysaccharide. Briefly, 30 mg (0.15 mmol) sodium alginate was dissolved in 10 mL of 8% acrylamide solution containing 0.48% MBA cross-linker. Then, 200 µL 10% APS and 10 µL TEMED were mixed in quickly, avoiding the formation of bubbles. The reaction mixture was then poured in between two pieces of glass with a 2-mm PDMS spacer and allowed to cure overnight. The hydrogel film was removed from the mold, equilibrated in deionized water for at least 6 h in order to extract any un-reacted material. Hydrogel discs of different sizes were cut from the film by using a biopsy punch, and specimens were dried overnight in an oven at 40° C., under atmospheric pressure. Xerogel discs were reconstituted by equilibrating them in the desired medium 6 hours prior to their use.

2.2.2. Characterization of Mechanical properties. Elastic and storage moduli were measured using a TA Instruments HR2-Discovery hybrid rheometer equipped with a peltier plate, and using parallel plates geometry. All measurements were conducted at 25.0° C. and all samples were conditioned at a constant force of 0.1 N and kept immersed in water during the analysis. Storage moduli were measured in the shear mode. 8 mm diameter hydrogel discs were sheared at 1 Hz, with a constant strain of 5%. Elastic moduli were measured in the axial compression mode; hydrogel discs were compressed from 1.0-5.0% axial strain at 1 Hz.

2.2.3. Photochemical Treatment of hydrogels. In order to induce photochemical responsiveness in these materials, hydrated hydrogel discs were soaked in a 100 mM $FeCl_3$ solution for at least 6 hours, unless otherwise stated. The orange iron-coordinated hydrogels (Fe-AlgAam) were irradiated with a 405 nm (146.7 $mW/cm^2$) LED lamp (Thorlabs). The iron was extracted from the irradiated samples by treating them with a 25 mM EDTA solution to give colorless gels. The chelating solution was changed 3 times during a 24-hour extraction period to assure the complete removal of the iron form the samples, yielding the sodium form of the gel (Na-AlgAam).

2.2.4. Electron Microscopy. Hydrogel samples were freeze-dried and sputter coated with Au/Pd. Secondary electron images were acquired in a Hitachi S2700 scanning electron microscope at 15 kV. Average pore diameters were measured using ImageJ software (National Institute of Health)

2.2.5. Attachment of RGD peptides. In a normal experiment, twenty 8 mm-diameter hydrogel discs were placed in a vial containing 8 mL 50 mM MES buffer, pH=6.5, containing 6.0 mg (52.13 µmol) of NHS. The gels were equilibrated for 10 minutes, before 1 mL 26 mM EDC in MES buffer was added. The reaction mixture was incubated for 15 min at room temperature before adding 1 mL of a 0.55 mM GGGRGDS (SEQ ID NO: 1) solution in H2O. The vials were placed on top of an orbital shaker and the left to react for 12 h. Finally, the reaction medium was aspirated and replaced with PBS buffer, and then deionized water. When complexation with Ca(II) was desired, hydrogels were soaked in a $CaCl_2$ solution for 6 h and then rinsed with deionized water. The functionalized gels were dried and stored until needed. When bigger gel discs were used, the amounts were scaled up based on the total surface area of the substrates. In cases when the peptide was attached to the gel before the photochemical treatment, we observed poor adhesion of the cells to the surface of the irradiated gels, suggesting that the peptide moieties were labile upon irradiation in presence of Fe(III). Thus, the peptide modification was performed only after the photochemical treatment and removal of the iron were accomplished.

2.2.6. Hydrolytic degradation. Degradation experiments were performed at pH=7.4 in PBS buffer, 2 mM in $NaN_3$. Each acellular hydrogel specimen was lyophilized and its dry weight recorded. Then, each sample was incubated in 2 mL medium at 37° C. for selected times, after which the medium was replaced with deionized water several times in a 2-hour period, and the sample was lyophilized before recording its final weight.

2.2.7. Diffusion kinetics. Briefly, a dry gel disc was swollen in 100 µL of 2 mg/mL solution of Texas red-labeled dextran. After equilibrating overnight, the loaded hydrogel was carefully removed from the solutions and rinsed. The amount of dextran encapsulated was determined from the decrease of the fluorescence in this solution. The loaded gels were then incubated in 1 mL PBS buffer, pH=7.4, and the supernatants were collected after increasing incubation times to measure the fluorescence intensity ($\lambda_{ex}$=595 nm/$\lambda_{em}$=615 nm). The supernatants were replaced with fresh PBS buffer at each time point. The emission spectra were recorded at a right angle to the direction of the excitation, on a PTI QuantaMaster spectrofluorometer with 1 nm resolution and 3s integration time. To determine the kinetics, the emission intensities were fitted to a first order exponential equation 1:[24]

$$\frac{W_t}{W\infty} = kt^n \qquad \text{eq. 1}$$

Where $W_t$ is the mass of the release solute at a given time, WW is the total mass of the encapsulated solute, k is a constant incorporating information about the macromolecular network and the released molecule,[24] and n is the kinetic exponent that can be related to the type of mechanism of the release.[24] In order to make a valid approximation, the values were considered only below 60% of the fractional release. Following this approach, the kinetic exponents were calculated assuming diffusion from a cylindrical sample.

2.2.8. Cell Culture. ATDC5 cells were obtained from a commercial source (ATCC Cell Lines, Manassas, Va.) at passage 11. Cells were expanded in standard growth media—Dulbecco's modified Eagle's medium (DMEM/F-12; Life. Technologies, Grand Island, N.Y.) supplemented with 5% fetal bovine serum (FBS; Life Technologies) and 1% penicillin/streptomycin antibiotics (Sigma). Cells were incubated at 37° C., 5% $CO_2$, and used between passages 17 and 22. For routine culture, medium was changed every other day and cells were harvested at 85% confluence with 0.05% Trypsin EDTA (Life Technologies). For differentiation studies, cells were grown on hydrogels in a differentiation medium consisting of DMEM/F-12 supplemented with 5% FBS, 1% antibiotics, 1% ITS+premix (final concentration: 6.25 µg/mL bovine insulin, 6.25 µg/mL transferrin, BD Biosciences, San Jose, Calif.), and 25 µg/mL ascorbic acid 2-phosphate (Sigma). Media were changed three times per week.

2.2.9. Live/dead Assay. 24 h post-seeding, the viability of ATDC5 cells cultured on hydrogels was assessed using a live/dead cytotoxicity kit (Molecular Probes, Eugene, Oreg.). Fluorescent images were taken using an Olympus inverted microscope.

2.2.10. Biochemical Analysis. To assess matrix production by ATDC5 cells cultured on hydrogels, sulfated glycosaminoglycan (sGAG) content was measured using the dimethylmethylene blue (DMMB; Sigma Chemicals) dye binding assay with shark chondroitin sulfate (0-50 mg/mL) as a standard using previously developed methods.[25] The results were normalized to DNA content. DNA content was quantified using Hoechst 33258 dye (Sigma) as described by Kim et al.[26]

On day 14, samples were digested with proteinase K (Roche, Germany) in a buffer containing 0.1M sodium acetate at 56° C. for 16 h. Samples were then added to DMMB solution at a ratio of 1:10, mixed and the absorbance was read at 595 and 525 nm. The ratio of the two photometric readings was averaged and converted to µg of sGAG based on a standard curve of chondroitin sulfate.

2.2.11. Statistical Analysis

Results are reported as the mean±standard deviation. The Student's T test and the ANOVA1 function of the Igor Pro software (WaveMetrics) were used to evaluate the data; values of $p \leq 0.05$ were considered statistically significant. Values of $p \leq 0.01$ are marked as , values of $p \leq 0.001$ are marked as .

3. Results and Discussion

By incorporating alginate into acrylamide hydrogels we introduce a responsiveness that was not present in pure Paam hydrogels. The acrylic polymer gave mechanical and chemical stability to the material, while the polysaccharide gave the possibility of creating new chemical interactions including responding to pH changes and coordinating to metal ions. The interaction of the polysaccharide carboxylates with Fe(III) ions was evidenced by both a change from colorless to orange and an increase in stiffness, as the ferric ions diffused into the gels and new coordinative crosslinking points were created (FIG. 17A). Based on these results, we fixed the contact time between the hydrogels in the Fe(III) solution to 6 h for the rest of our experiments. Exposure of these materials to visible light (405 nm or 450 nm) induced a drop in the elastic modulus of the gels as the Fe(III) was photoreduced. A concomitant oxidative decarboxylation of the polysaccharide has been reported to happen during the photoreaction; yielding a material with a lower carboxylate content and shorter polysaccharide chains.[19, 23, 27]

Figure 18:
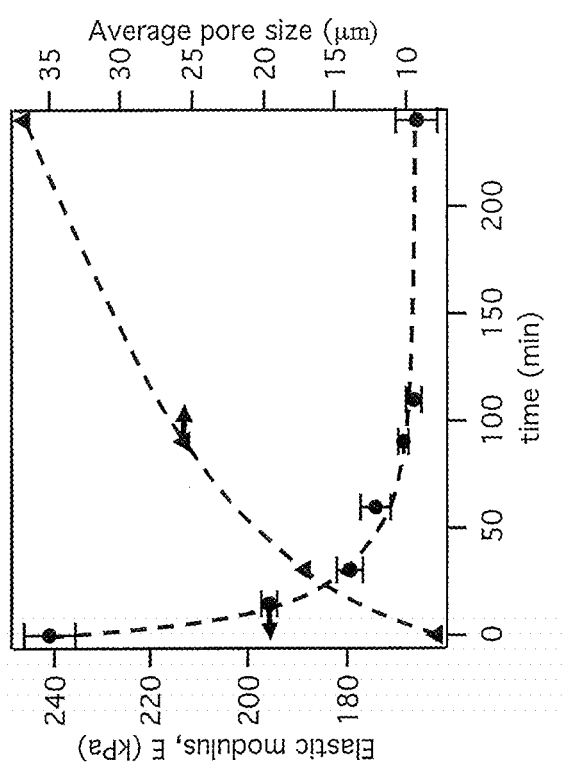
FIG. 18 shows changes in elastic modulus and microstructure upon irradiation of Fe-AlgAam hydrogels for an embodiment of the invention.
Figure 17:
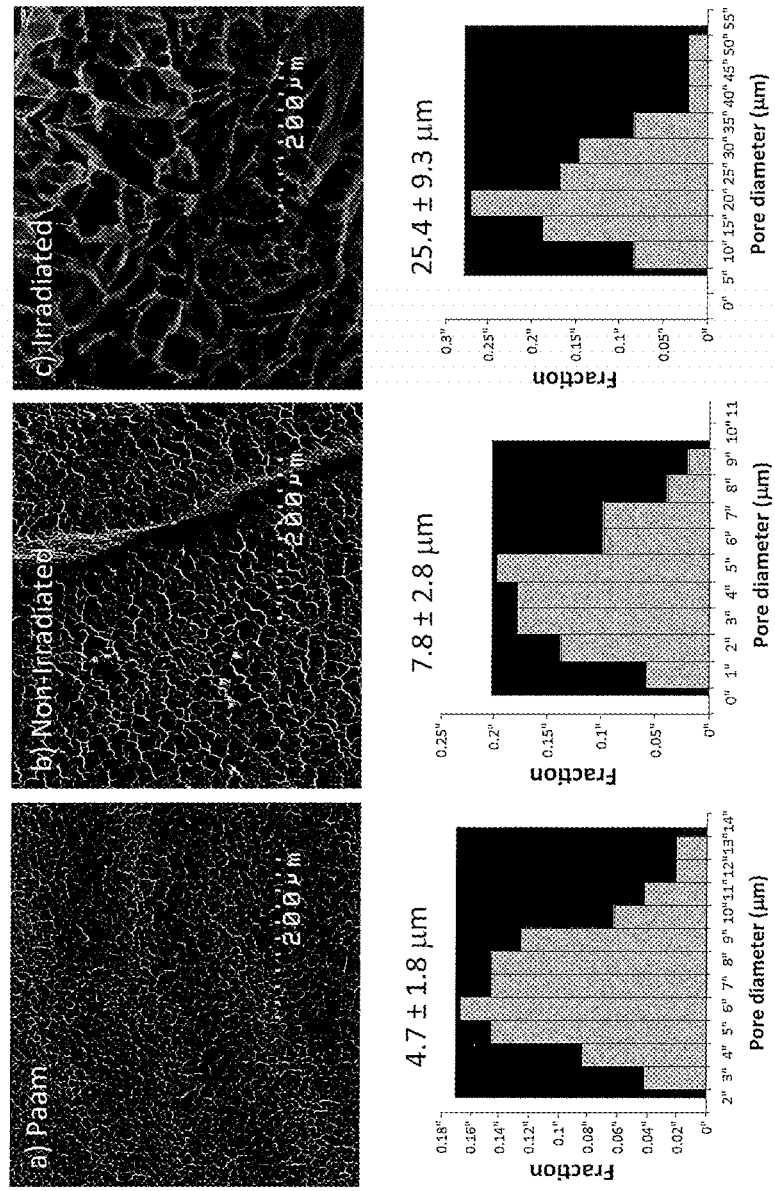
FIG. 17 shows interaction of the polysaccharide carboxylates with Fe(III) ions in accordance with an embodiment of the invention.

FIG. 17 a) Evolution of the elastic modulus of AlgAam gels as a function of the contact time with 100 mM $FeCl_3$. b) % change in the elastic modulus of the irradiated vs. non-irradiated gels in the Fe(III), Na(I) and Ca(II) forms. Although the photoreaction affected mainly the polysaccharide segments of the material, it produced irreversible changes on the microstructure of the gel, and therefore in the mechanical properties of the bulk. As we reported previously, a systematic drop in elastic modulus of the Fe-AlgAam gel upon irradiation, was observed and maintained after the transition metal was exchanged for Ca(II) or Na(I) (FIG. 18). Furthermore, the difference in modulus before and after irradiation was less important in Na-AlgAam than in Ca-AlgAam, which can be attributed to the secondary crosslinking of the carboxylate groups by divalent calcium, but not by the monovalent sodium ions. The results presented in FIG. 6 indicate that the final modulus of the irradiated hydrogel was easily adjusted by changing the time of exposure to light. For the purpose of this work, we fixed the irradiation time to 90 min, as we wanted to evaluate the change induced in these materials upon irradiation. Fe-containing gels irradiated for 90 min presented a 30% drop in the compressive elastic modulus. Again, the difference between the irradiated and non-irradiated sample was only 8% after exchanging the Fe(III) for sodium ions, while the addition of Ca(II) enhanced the difference up to 15% (FIG. 17) due to the differences in cross-linking from coordination of the Ca(II) compared to non-coordinated Na+.

FIG. 19. Top: SEM micrographs showing differences in the microstructure of a) Paam, b) Non-irradiated, and c) 90 min Irradiated AlgAam hydrogels in the sodium form, after conjugation with the GGGRGDS (SEQ ID NO: 1)-peptide. Bottom: the corresponding pore size distribution histograms The photochemical treatment also caused an increase in the pore size of the gels (FIG. 19). With an initial average of 7.8 µm, the overall pore diameter increased to 25.4 µm after 90 min irradiation (FIG. 19). Although these dimensions are determined in dried samples via electron microscopy and can be different from those in the hydrated gels, the trend is expected to be the same.

Figure 20:
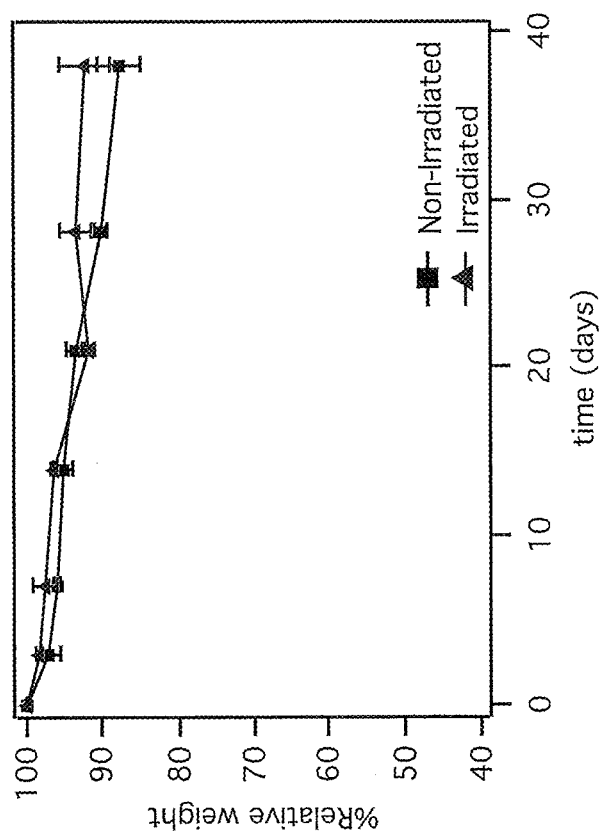
FIG. 20 shows hydrolytic stability of AlgAam samples upon incubation, for an embodiment of the invention.

This ability to tune the pore size in the gels is important for tissue engineering. It was reported that when cartilage cells are cultured on cross-linked gelatin gels, the materials with the smaller pores favored cell growth rather than ECM production.[28] In a different study, marrow stromal cells cultured on polyethylene glycol hydrogels with variable porosity; only those cells growing in the most porous scaffolds became consolidated with osteogenesis progression of cell diferentiation.[29] Given the change in porosity caused by the photochemical treatment of AlgAam gels, we expect this difference in micro-architecture between the two conditions (dark vs. irradiated) to have important consequences in the performance of these materials as substrates for tissue engineering, The hydrolytic stability of Na-AlgAam hydrogels was assessed in PBS (pH=7.45 at 37° C.), simulating the conditions of a tissue culture (FIG. 20). The results showed that after 14 days of incubation the weight loss in both materials was around 5%. However, when studying the supernatants by 1H-NMR, we were not able to see any significant signal corresponding to any soluble hydrolysate. A similar study reported for AlgAam hydrogels, used the crosslinking density, gel volume, and Young's modulus as indicators for degradation of the material showing no significant relationship between these properties and the incubation time, over a period of 50 days.[13]

To increase the shelf life of these materials as substrates for tissue engineering, we studied the potential storage of the samples in the dry state (xerogels) and reconstitution in aqueous media. The storage modulus of both the irradiated and non-irradiated materials was not affected after 4 processing cycles (FIG. 21) These results allowed us to conveniently prepare batches of samples and store them as dry discs that were successfully hydrated in the desired media only when needed. Being able to have hydrogel scaffolds in this "dormant" state ensures the reproducibility of our experiments, as rules out changes in the matrix structure due to hydrolytic processes. It also presents an opportunity for easy transport of the scaffolds, which can then be easily re-hydrated with cell suspensions.

Figure 21:
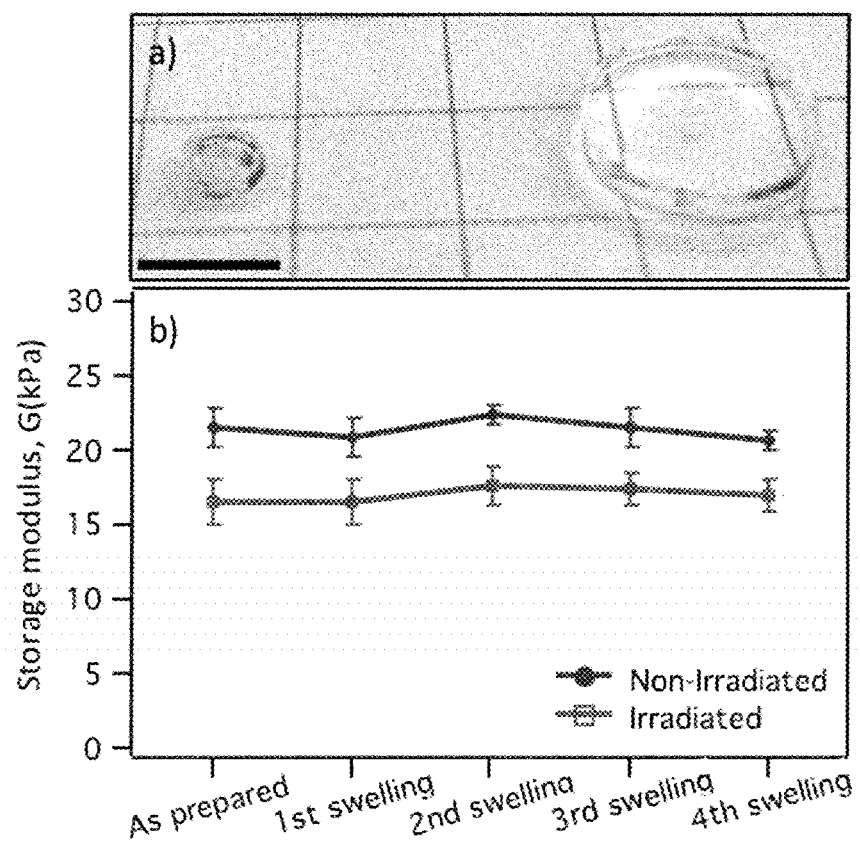
FIG. 21 shows storage modulus of both the irradiated and non-irradiated materials, for an embodiment of the invention.

FIG. 21. a) Dehydrated and reconstituted forms of AlgAam (Scale bar is 5 mm). b) Effect of dehydration-reconstitution cycles on the storage modulus of Na-AlgAam gels.

Figure 22:
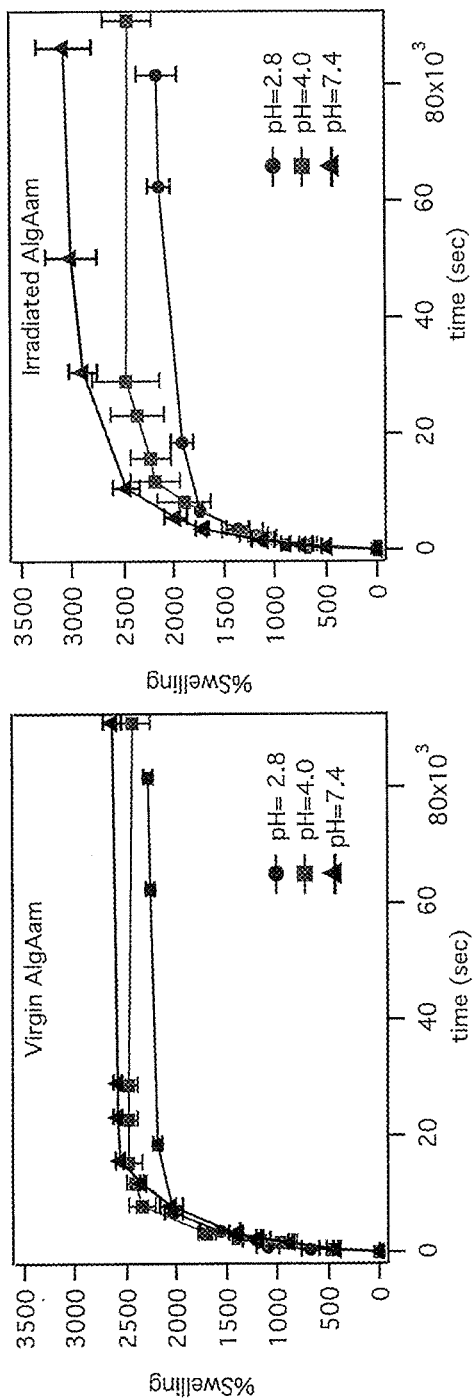
FIG. 22 shows swelling profiles of virgins and irradiated AlgAam gels at different pH in an embodiment of the invention.

To study the swelling behavior and transport dynamics in these hydrogels, dynamic swelling experiments were performed at different pH. Different diffusional coefficients were calculated from the swelling isotherms (FIG. 22) and used to characterize the water transport mechanism. According to the theory, for a cylindrical sample n=0.45 if the diffusion follows a Fickian mechanism,[24] that is, the diffusion rate is much lower than the rate of relaxation of the polymeric chains.[30,31] In cases where 0.45>n>1, the transport is non-Fickian or anomalous, and when n=1 the process is said to be diffusion controlled and independent of time.[26] Our results indicate a similar, but not identical, swelling behavior for both conditions (irradiated and non-irradiated) (FIG. 22 and Table 3). Hydration of the gels was a non-Fickian process, and occurred faster at pH=7.4 than at pH=4.0 or pH=2.8. Also important to notice, was a higher equilibrium swelling in the irradiated gels, which we attributed to breakage of the covalent hydrogel network upon irradiation, rendering the polymer chains more flexible, and therefore, more susceptible to swelling. When the pH of the medium was lower than the pKa of alginate (pKa mannuronic acid=3.38, pKa guluronic acid=3.65)[32] the kinetic exponent was lower than the value expected for a Fickian diffusion (Table 3). At this pH the carboxylate groups in alginate were protonated and the swelling of the gels was poor. The observed slow swelling for both the virgin and the irradiated gels indicated that, even after the photo-degradation of the polysaccharide, there were significant numbers of carboxylate groups remaining as to maintain a sharp response to pH.

Figure 23:
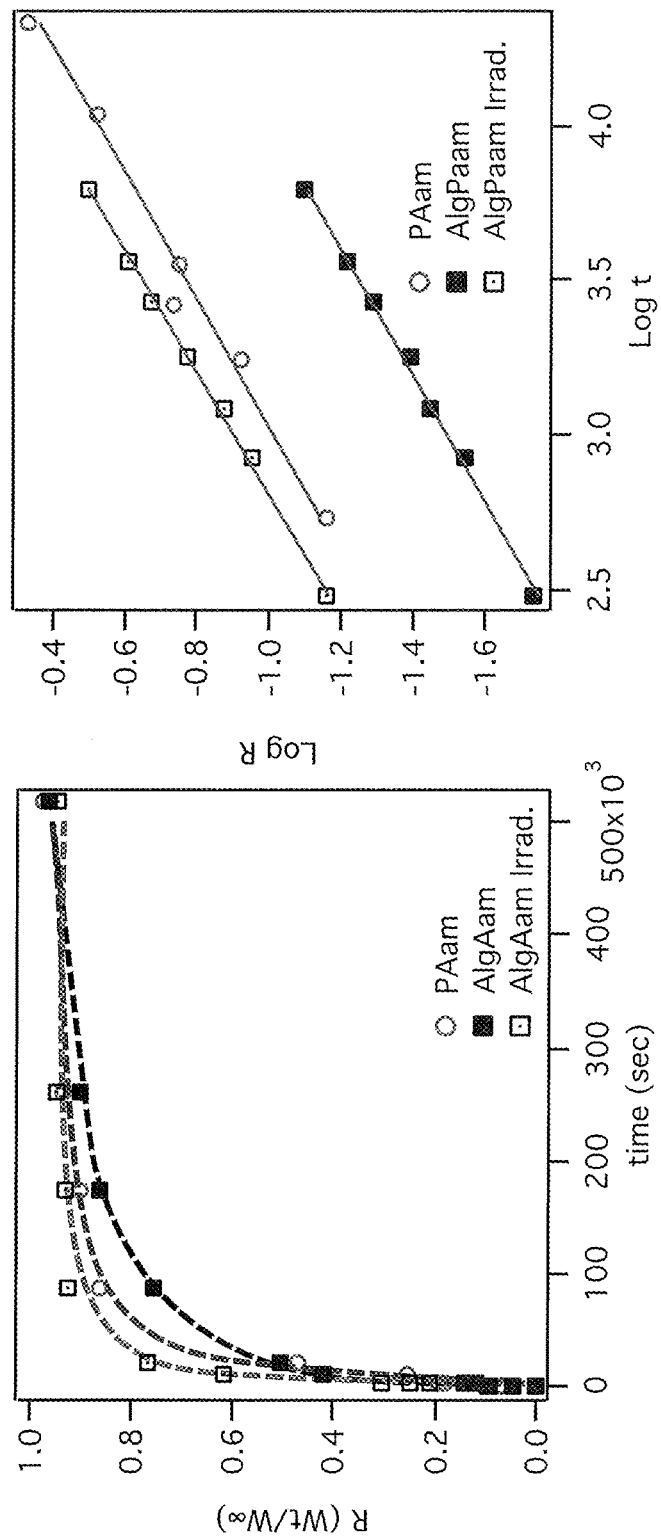
FIG. 23 shows the transport properties of hydrogels in an embodiment of the invention.

FIG. 23 a) Release profile (R) of the labeled dextran from hydrogel discs in PBS at 25° C. b) Linear fit lines of Log R Vs Log t for the different gels. The transport properties of these gels were further evaluated in PBS, pH=7.4, using Texas Red-labeled dextran (70 kDa) as a fluorescent probe. Dextran has been used as model to study solute release mechanism in hydrogel systems,[33,34,35] and the reported hydrodynamic radius for the specific molecular size used here was between 10-14 nm, as measured by light scattering.[36] The diffusion of the polymer occurred faster in the irradiated AlgAam than in the non-treated gel or pure Paam (FIG. 23A), and fitting of the release profile to $kt^n$ shows differences in the diffusion coefficients (slope) (FIG. 23B). The study of the diffusion kinetics suggested a more diffusion-controlled transport of the dextran in the irradiated gel (n=0.55), than in the case of the non-irradiated gel or Paam (n=0.45 and 0.46, respectively) (Table 4). The difference in the diffusion exponents was statistically significant and suggests a change in the transport properties, which agrees with the higher pore size and lower crosslinking density of the irradiated gel. Given the avascular nature of cartilage, small changes in the transport properties are expected to play important roles in the performance of the synthetic substrate, as processes such as nutrient diffusion or metabolic waste removal are affected.[37]

Decoration of the AlgAam hydrogels with an adhesion promoting peptide sequence was necessary to ensure the successful interaction of ATDC5 cells with the material. The peptide was conjugated after the photochemical reaction and complete removal of iron from the sample to avoid undesired reactions during the photochemical treatment. Using this method, cells adhered to the surface of the materials after incubation for only a few minutes.

Figure 24:
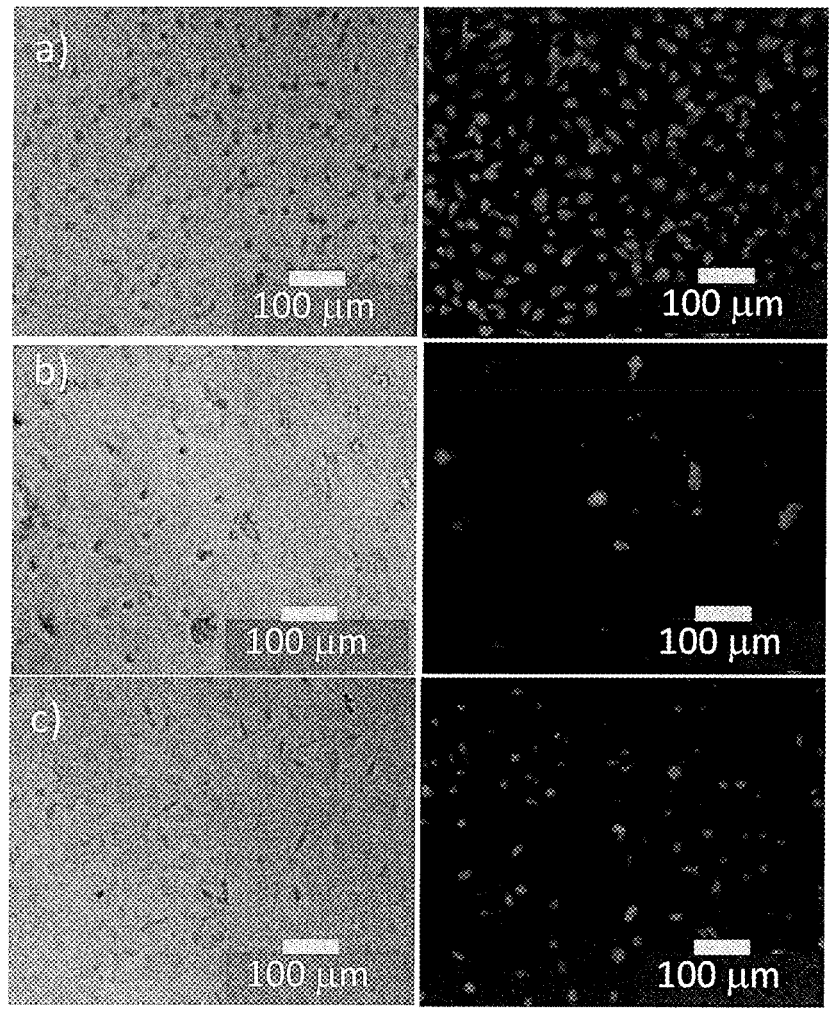
FIG. 24 shows brightfield (left) and live/dead fluorescent (right) images of ATDC5 cells in accordance with an embodiment of the invention.

FIG. 24. Brightfield (left) and live/dead fluorescent (right) images of ATDC5 cells after 24 h culture on a) Tissue Culture Plastic (control), b) Non-irradiated Na-AlgAam, and c) 90 min-irradiated Na-AlgAam.

The biocompatibility of similar materials has been reported for D1 mouse mesenchymal stem cells, and in-vivo implantation in mice; showing very low cytotoxicity.13 ATDC5 cells seeded onto irradiated and non-irradiated AlgAam gels were 80-85% viable after 1 day of culture, further demonstrating the biocompatibility of this material (FIG. 24). Detailed examination of the micrographs in FIG. 24 also reveals a better adhesion interaction of the cells with the surface of the irradiated gels, reaching a density of $2.95 \times 10^4$ cell/cm$^2$ compared to $1.53 \times 10^4$ cell/cm$^2$ in the non-irradiated gels.

Figure 25:
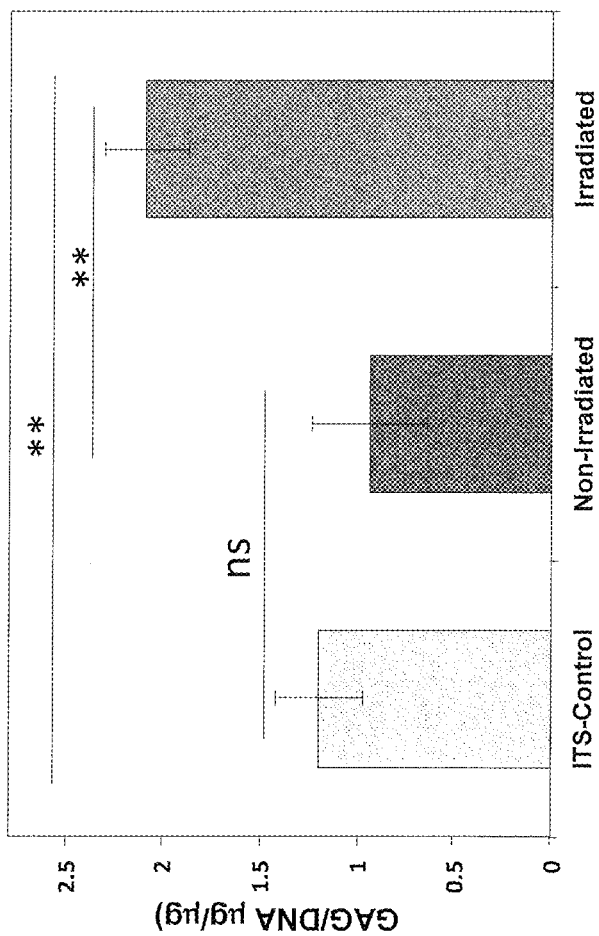
FIG. 25 shows sulphated-glycosaminoglycan (sGAG) production in ATDC5 cell in accordance with an embodiment of the invention.

FIG. 25 Sulphated-glycosaminoglycan (sGAG) production in ATDC5 cells cultured for 14 days. P<0.05, n=3, 4 samples/condition. To assess the potential of these materials for cartilage tissue engineering, chondroprogenitor cells were cultured on hydrogels and kept in differentiation media for 14 days. Sulfated glycosaminoglycan (sGAG) production, a hallmark of chondrogenesis,[38] was measured evaluated. The results revealed that matrix production in cells cultured on irradiated gels was significantly higher than that of cells cultured on either non-irradiated gels or tissue culture plastic (control) (FIG. 25).

CONCLUSIONS

We presented the photochemistry of Fe-AlgAam as a tool for changing the micro and macroscopic properties of these soft materials. These hydrogels become softer and more porous upon irradiation, presenting changes in their swelling and transport properties. We studied the effect that dehydration has on the mechanical properties of the gels, concluding that these materials can be successfully dehydrated and reconstituted without any significant change in mechanical properties; this is important to us, since a long storage of the scaffolds in aqueous conditions would compromise the structure of the material, as we describe in the hydrolytic stability study. Our results confirm the suitability of these materials as substrates for cell culture, which are able to support ATDC5 cell chondrogenesis and ECM production. The most noteworthy result of our work is the effect that the photochemical treatment of the gel had on the development of the growing cells, boosting the production of proteoglycans, probably due to the lower stiffness and higher porosity of the treated gel. Future work will focus on using this photochemical method for the creation of specific patterns and gradients of mechanical properties in order to mimic natural matrixes and improve the quality of the cultured tissue.

1. Methods 1.1 Dynamic changes in mechanical properties upon irradiation. Square 1.5 cm×1.5 cm hydrogel specimens were soaked in a freshly prepared $FeCl_3$ solution for 6 h before illuminating them with 405 nm Light (146.7 mW/cm$^2$) for different amounts of time. Special care was taken in order to avoid differences in the specimen size due to the network shrinking upon coordination with metals; therefore, the gels were cut right before the measurement was performed. For the Fe-AlgAam samples, the gels were rinsed with DI water and 8-mm discs were punch-cut and tested in the rheometer. For the Na-AlgAam samples, irradiated and non-irradiated Fe-containing gels were treated with 0.025 M $Na_2$-EDTA solution to remove the iron; only then, hydrogel discs were cut and tested. As for the Ca-AlgAam samples, these were obtaining upon soaking the previously obtained Na-AlgAam samples in a 0.1 M $CaCl_2$ solution for 6 h.

1.2. Hydrolytic degradation. Degradation experiments were performed at pH=7.4 in PBS buffer, 2 mM in $NaN_3$. Each acellular hydrogel specimen was lyophilized and its dry weight recorded. Then, each sample was incubated in 2 mL medium at 37° C. for a given time, after which the medium was replaced with deionized water several times in a 2-hour period, and the sample was lyophilized before recording its final weight.

To evaluate the degradation mechanism, a series of hydrogel samples were incubated in deuterated PBS, pH=7.4, 2 mM $NaN_3$ and 1H-NMR spectra of the supernatants were collected at different time points over a 1 month period.

1.3 Swelling experiments. Dynamic swelling experiments were performed by incubating dried Na-AlgAam specimens in the swelling medium at 37° C. and measuring their weight gain as a function of time. The gels were removed from the medium and blot dried with a filter paper before weighing.

1.3 Swelling experiments. Dynamic swelling experiments were performed by incubating dried Na-AlgAam specimens in the swelling medium at 37° C. and measuring their wright gain as a function of time. The gels were removed from the medium and blot fried with a filter paper before weighing.

To study the swelling kinetics, the degree of swelling as a function of time was fitted to the following exponential equation:[24]

$$\frac{W_t}{W\infty} = kt^n \quad \text{eq. 1}$$

Where $W_t$ is the mass of solvent absorbed by the gel at a given time, $W\infty$ is the total mass of the solvent at the equilibrium, k is a constant incorporating information about the macromolecular network and the released molecule,[25] and n is the kinetic exponent that can be related to the mechanism of the diffusion.

The degree of swelling was calculated from equation 2.

$$\% S = \frac{W_t - W_o}{W_o} \quad \text{eq. 2}$$

The effect that successive cycles of dehydration-reconstitution have on the properties of these gels was studied by subjecting a series of samples to consecutive steps of oven drying (12 h) and rehydration in PBS (6 h). 1.4 Photosensitivity of Fe(III)-GGGRGDS (SEQ ID NO: 1). The reactivity of the adhesion promoting peptide in the presence of ferric ions and light was evaluated by irradiating a solution that was 0.5 mM in the peptide and 0.5 mM in $Fe(NO_3)_3$. Briefly, 1 mL of this solution was placed in a quartz cuvette and irradiated with 2.5 mW of 405 nm LED light (ThorLabs) for different increasing amounts of time. The absorbance of the solution was measured after each irradiation period and the amount of photoreduced iron was determined from the absorbance of the Fe(II) complex with 1,10-phenanthroline. The quantum yield of the reaction (0) was calculated as the moles of Fe(III) photoproduced per mol of photon absorbed by the sample.

Figure 15:
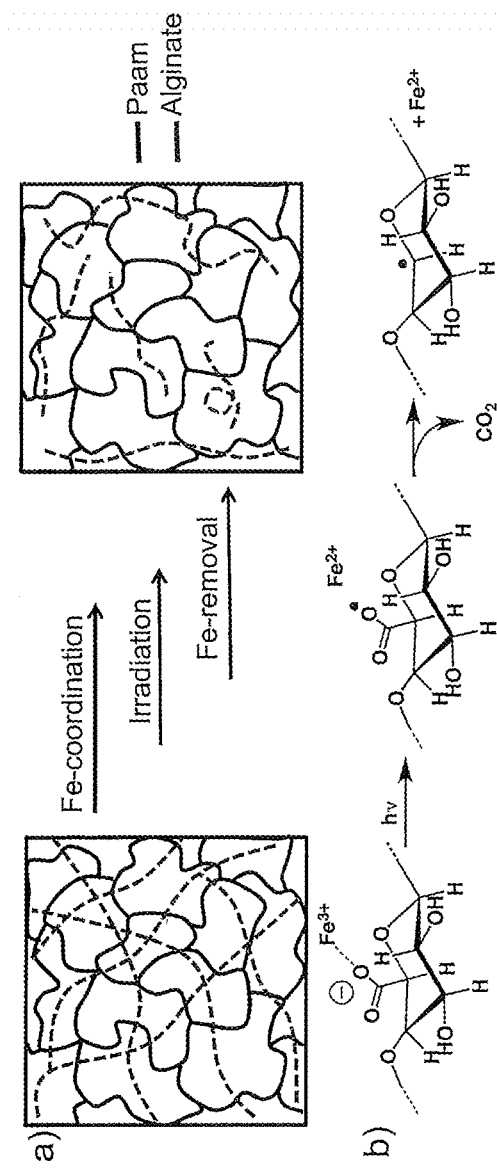
FIG. 15 shows degradation of the alginate segments upon application of the photochemical treatment in an embodiment of the invention.

FIG. 15 a) Degradation of the alginate segments upon application of the photochemical treatment. b) Photodecarboxylation of the Fe-alginate complex is the main reaction involved in the process.

FIG. 18. Changes in elastic modulus and microstructure upon irradiation (405 nm light, 146.72 mW/cm$^2$) of Fe-AlgAam hydrogels. The average pore size was measured by SEM from the gels after iron removal by EDTA.

FIG. 20. Hydrolytic stability of AlgAam samples upon incubation in PBS, pH=7.4, at 37±1° C. The difference in weight loss is not significant for the irradiated and non-irradiated gels.

FIG. 22 Swelling profiles of virgins and irradiated AlgAam gels at different pH.

Figure 26:
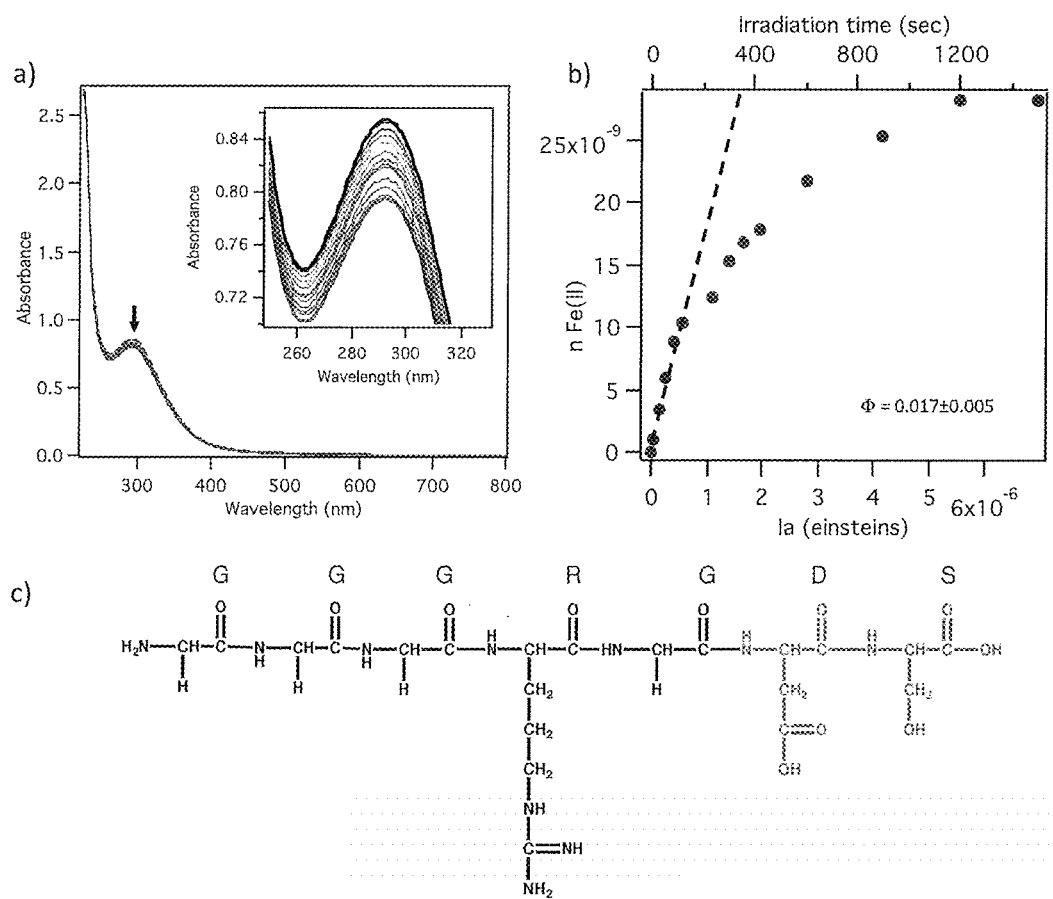
FIG. 26 shows a preliminary photochemical study of Fe(III)-GGGRGDS (SEQ ID NO: 1) in accordance with an alternative embodiment of the invention.

FIG. 26 Preliminary photochemical study of Fe(III)-GGGRGDS (SEQ ID NO: 1). a) Evolution of the absorption spectrum upon irradiation. b) Photogeneration of Fe(II) per mol of photons (einsteins). The quantum yield of the reaction was determined from the slope of the linear part of the curve. c) Primary structure of the adhesion-inducing peptide. The amino acids in red indicate free carboxylate groups that can coordinate Fe(III) ions.

REFERENCES FOR EXAMPLE 2

(1) Drury, J. L.; Mooney, D. J. Hydrogels for Tissue Engineering: Scaffold Design Variables and Applications. Biomaterials 2003, 24, 4337-4351.

(2) TelRmar, J.; Brandl, F.; Gopferich, A. Hydrogels for Tissue Engineering. In Fundamentals of Tissue Engineering and Regenerative Medicine; Meyer, U.; Handschel, J.; Wiesmann, H. P.; Meyer, T., Eds.; Springer Berlin Heidelberg, 2009; pp. 495-517.

(3) Higuchi, A.; Ling, Q.-D.; Chang, Y.; Hsu, S.-T.; Umezawa, A. Physical Cues of Biomaterials Guide Stem Cell Differentiation Fate. Chem. Rev. 2013, 113, 3297-3328.

(4) Engler, A. J.; Griffin, M. A.; Sen, S.; Bönnemann, C. G.; Sweeney, H. L.; Discher, D. E. Myotubes Differentiate Optimally on Substrates with Tissue-like Stiffness: Pathological Implications for Soft or Stiff Microenvironments. J. Cell Biol. 2004, 166, 877-887.

(5) Lee, J.; Abdeen, A. A.; Zhang, D.; Kilian, K. A. Directing Stem Cell Fate on Hydrogel Substrates by Controlling Cell Geometry, Matrix Mechanics and Adhesion Ligand Composition. Biomaterials 2013, 34, 8140-8148.

(6) Discher, D. E.; Janmey, P.; Wang, Y. Tissue Cells Feel and Respond to the Stiffness of Their Substrate. Science 2005, 310, 1139-1143.

(7) Engler, A. J.; Sen, S.; Sweeney, H. L.; Discher, D. E. Matrix Elasticity Directs Stem Cell Lineage Specification. Cell 2006, 126, 677-689.

(8) Annabi, N.; Nichol, J. W.; Zhong, X.; Ji, C.; Koshy, S.; Khademhosseini, A.; Dehghani, F. Controlling the Porosity and Microarchitecture of Hydrogels for Tissue Engineering. Tissue Eng. Part B Rev. 2010, 16, 371-383.

(9) Lien, S.-M.; Ko, L.-Y.; Huang, T.-J. Effect of Pore Size on ECM Secretion and Cell Growth in Gelatin Scaffold for Articular Cartilage Tissue Engineering. Acta Biomater. 2009, 5, 670-679.

(10) Connon, C. J.; Hamley, I. W. Hydrogels in Cell-Based Therapies; Royal Society of Chemistry, 2014.

(11) Sun, J.-Y.; Zhao, X.; Illeperuma, W. R. K.; Chaudhuri, O.; Oh, K. H.; Mooney, D. J.; Vlassak, J. J.; Suo, Z. Highly Stretchable and Tough Hydrogels. Nature 2012, 489, 133-136.

(12) Hossein Omidian, J. G. R. Elastic, Superporous Hydrogel Hybrids of Polyacrylamide and Sodium Alginate. Macromol. Biosci. 2006, 6, 703-710.

(13) Darnell, M. C.; Sun, J.-Y.; Mehta, M.; Johnson, C.; Arany, P. R.; Suo, Z.; Mooney, D. J. Performance and Biocompatibility of Extremely Tough Alginate/polyacrylamide Hydrogels. Biomaterials 2013, 34, 8042-8048.

(14) Zhu, M.-L.; Li, Y.-L.; Zhang, Z.-M.; Jiang, Y. Preparation and Properties of Stretchable and Tough Alginate/polyacrylamide Hollow Capsules. RSC Adv. 2015, 5, 33262-33268.

(15) Yang, C. H.; Wang, M. X.; Haider, H.; Yang, J. H.; Sun, J.-Y.; Chen, Y. M.; Zhou, J.; Suo, Z. Strengthening Alginate/polyacrylamide Hydrogels Using Various Multivalent Cations. ACS Appl. Mater. Interfaces 2013, 5, 10418-10422.

(16) Şolpan, D.; Torun, M. (Sodium Alginate/Acrylamide) Semi-Interpenetrating Polymer Networks and Their Usability on Removal of Lead, Cadmium, Nickel Ions. J. Macromol. Sci. Part A 2005, 42, 1435-1449.

(17) Tripathi, R.; Mishra, B. "Development and Evaluation of Sodium Alginate-Polyacrylamide Graft-Co-Polymer-Based Stomach Targeted Hydrogels of Famotidine." AAPS Pharm Sci Tech 2012, 13, 1091-1102.

(18) Low, Z. W.; Chee, P. L.; Kai, D.; Loh, X. J. The Role of Hydrogen Bonding in Alginate/poly(acrylamide-Co-Dimethylacrylamide) and Alginate/poly(ethylene Glycol) Methyl Ether Methacrylate-Based Tough Hybrid Hydrogels. RSC Adv. 2015, 5, 57678-57685.

(19) Giammanco, G. E.; Ostrowski, A. D. Photopatterning the Mechanical Properties of Polysaccharide-Containing Gels Using Fe3+ Coordination. Chem. Mater. 2015, 7 3068-3076.

(20) Guo, P.; Yuan, Y.; Chi, F. Biomimetic Alginate/polyacrylamide Porous Scaffold Supports Human Mesenchymal Stem Cell Proliferation and Chondrogenesis. Mater. Sci. Eng. C 2014, 42, 622-628.

(21) Li, J.; Illeperuma, W. R. K.; Suo, Z.; Vlassak, J. J. Hybrid Hydrogels with Extremely High Stiffness and Toughness. ACS Macro Lett. 2014, 3, 520-523.

(22) Giammanco, G. E.; Sosnofsky, C. T.; Ostrowski, A. D. Light-Responsive Iron(III)-Polysaccharide Coordination Hydrogels for Controlled Delivery. ACS Appl. Mater. Interfaces 2015, 7, 3068-3076.

(23) Okajima, M. K.; Ie Nguyen, Q. T.; Tateyama, S.; Masuyama, H.; Tanaka, T.; Mitsumata, T.; Kaneko, T. Photoshrinkage in Polysaccharide Gels with Trivalent Metal Ions. Biomacromolecules 2012, 13, 4158-4163.

(24) Ritger, P. L.; Peppas, N. A. A Simple Equation for Description of Solute Release I. Fickian and Non-Fickian Release from Non-Swellable Devices in the Form of Slabs, Spheres, Cylinders or Discs. J. Controlled Release 1987, 5, 23-36.

(25) Coleman, R. M.; Case, N. D.; Guldberg, R. E. Hydrogel Effects on Bone Marrow Stromal Cell Response to Chondrogenic Growth Factors. Biomaterials 2007, 28, 2077-2086.

(26) Kim, Y. J.; Sah, R. L.; Doong, J. Y.; Grodzinsky, A. J. Fluorometric Assay of DNA in Cartilage Explants Using Hoechst 33258. Anal. Biochem. 1988, 174, 168-176.

(27) Giammanco, G. E.; Sosnofsky, C. T.; Ostrowski, A. D. Light-Responsive Iron(III)-Polysaccharide Coordination Hydrogels for Controlled Delivery. ACS Appl. Mater. Interfaces 2015.

(28) Effect of pore size on ECM secretion and cell growth in gelatin scaffold for articular cartilage tissue engineering. Acta Biomater. 2009, 5, 670-679.

(29) Dadsetan, M.; Hefferan, T. E.; Szatkowski, J. P.; Mishra, P. K.; Macura, S. I.; Lu, L.; Yaszemski, M. J. Effect of Hydrogel Porosity on Marrow Stromal Cell Phenotypic Expression. Biomaterials 2008, 29, 2193-2202.

(30) Halah, A. E.; Contreras, J.; Rojas-Rojas, L.; Rivas, M.; Romero, M.; López-Carrasquero, F. New Superabsorbent Hydrogels Synthesized by Copolymerization of Acrylamide and N-2-Hydroxyethyl Acrylamide with Itaconic Acid or Itaconates Containing Ethylene Oxide Units in the Side Chain. J. Polym. Res. 2015, 22, 1-10.

(31) Kim, B.; La Flamme, K.; Peppas, N. A. Dynamic Swelling Behavior of pH-Sensitive Anionic Hydrogels Used for Protein Delivery. J. Appl. Polym. Sci. 2003, 89, 1606-1613.

(32) Rehm, B. H. A. Alginates: Biology and Applications: Biology and Applications; Springer Science & Business Media, 2009.

(33) Singh, R. K.; Seliktar, D.; Putnam, A. J. Capillary Morphogenesis in PEG-Collagen Hydrogels. Biomaterials 2013, 34, 9331-9340.

(34) Rosenberg, R. T.; Dan, N. R. Controlling Surface Porosity and Release from Hydrogels Using a Colloidal Particle Coating. J. Colloid Interface Sci. 2010, 349, 498-504.

(35) Carrion, B.; Souzanchi, M. F.; Wang, V. T.; Tiruchinapally, G.; Shikanov, A.; Putnam, A. J.; Coleman, R. M. The Synergistic Effects of Matrix Stiffness and Composition on the Response of Chondroprogenitor Cells in a 3D Precondensation Microenvironment. Adv. Healthc. Mater. 2016.

(36) Choi, J. J.; Wang, S.; Tung, Y.-S.; Morrison, B.; Konofagou, E. E. Molecules of Various Pharmacologically-Relevant Sizes Can Cross the Ultrasound-Induced Blood-Brain Barrier Opening in Vivo. Ultrasound Med. Biol. 2010, 36, 58-67.

(37) Chung, C.; Beecham, M.; Mauck, R. L.; Burdick, J. A. The Influence of Degradation Characteristics of Hyaluronic Acid Hydrogels on in Vitro Neocartilage Formation by Mesenchymal Stem Cells. Biomaterials 2009, 30, 4287-4296.

(38) Heinegard, D. Proteoglycans and More—from Molecules to Biology. Int. J. Exp. Pathol. 2009, 90, 575-586.

TABLE 1

Compressive elastic moduli measured of Paam and Paam-UCPS gels

Elastic Modulus E' (KPa)

|     | Virgin  | Dark-Fe     | Irrad-Fe | Dark-EDTA   | Irrad-EDTA | Dark-Ca    | Irrad-Ca   |
|-----|---------|-------------|----------|-------------|------------|------------|------------|
| Aam | 112 ± 3 | 106.8 ± 0.2 | 104 ± 2  | 108.3 ± 0.8 | 100 ± 2    | 111 ± 2    | 93 ± 1     |
| Alg | 106 ± 2 | 247 ± 9     | 109 ± 2  | 102.1 ± 0.6 | 105 ± 2    | 146 ± 6    | 113 ± 2    |
| Pec | 115 ± 2 | 265.1 ± 0.5 | 92 ± 3   | 114 ± 0.6   | 84 ± 2     | 127 ± 1    | 84.3 ± 0.9 |
| Hya | 73 ± 2  | 100 ± 3     | 41 ± 2   | 73 ± 0.8    | 45 ± 1     | 87.7 ± 0.2 | 53.6 ± 0.7 |

TABLE 2

Dynamic shear moduli measured of Paam and Paam-UCPS gels

Storage Modulus G' (KPa)

|      | Virgin    | Fe Dark     | Fe Irrad    | Dark-EDTA  | Irrad-EDTA  | Dark-Ca   | Irrad-Ca    |
|------|-----------|-------------|-------------|------------|-------------|-----------|-------------|
| Aam  | 5.8 ± 0.4 | 6.6 ± 0.1   | 4.7 ± 0.3   | 6.0 ± 0.1  | 3.0 ± 0.2   | 4.9 ± 1   | 4.3 ± 0.1   |
| Alg  | 4.9 ± 0.2 | 12.5 ± 0.6  | 5.3 ± 0.1   | 5.0 ± 0.3  | 5.0 ± 0.1   | 7.5 ± 0.4 | 4.5 ± 0.1   |
| Pect | 3.4 ± 0.1 | 18.7 ± 0.1  | 2.33 ± 0.02 | 5.5 ± 0.2  | 2.61 ± 0.04 | 5.3 ± 0.4 | 2.39 ± 0.02 |
| Hya  | 2.0 ± 0.2 | 4.18 ± 0.07 | 0.38 ± 0.02 | 2.5 ± 0.1  | 0.43 ± 0.04 | 2.4 ± 0.1 | 1.2 ± 0.1   |

TABLE 3

AlgAam samples exposed our photochemical method for different times.

| Irradiation time | Elastic Modulus (kPa) | | | Average pore |
|---|---|---|---|---|
| (min)[a] | Fe(III) form | Na(I) form | Ca(II) form | size (μm)[b] |
| 0[c]   | 240 ± 5 | 111 ± 3.5 | 168 ± 3 | 7.8  |
| 15     | 195 ± 2 | 107 ± 4   | 149 ± 1 | —    |
| 30     | 179 ± 3 | 108 ± 3   | 145 ± 2 | 17.1 |
| 60     | 174 ± 3 | 100 ± 2   | 145 ± 2 | —    |
| 90[c]  | 168 ± 1 | 97 ± 5    | 143 ± 2 | 15.4 |
| 110    | 166 ± 2 | 101 ± 1   | 142 ± 3 | —    |
| 240    | 165 ± 4 | 100 ± 5   | 138 ± 2 | 36.7 |

[a] only the Fe(III) containing materials were exposed to light, both the Na(I) and Ca(II) forms were obtained by cationic exchange.
[b] Pore sizes were determined by SEM on samples after removing the iron with EDTA (sodium form of the gels)
[c] selected samples used in cell experiments.

TABLE 4

Diffusional exponents for the swelling experiments at different pH.

| | n | |
|---|---|---|
| pH | Virgin AlgAam | Irrad. AlgAam[a] |
| 2.8 | 0.23 | 0.23 |
| 4.0 | 0.56 | 0.47 |
| 7.4 | 0.54 | 0.58 |

[a] sample irradiated for 90 min.

TABLE 5

Diffusional exponents measured for the release of 70 KDa Dextran from AlgAam gels in PBS. $P \leq 0.05$ n = 3

| Sample | n |
|---|---|
| Paam | 0.46 ± 0.01 |
| Non-irradiated AlgAam | 0.45 ± 0.03 |
| Irradiated AlgAam[a] | 0.55 ± 0.04 |

[a] sample irradiated for 90 min.

What is claimed:

1. A method of creating patterns on a hydrogel, comprising the steps of:
   (i) forming a polyacrylamide-uronate-containing polysaccharide hydrogel;
   (ii) exposing the hydrogel to a $Fe^{3+}$ metallic cation that can be reduced, thereby creating a metal-coordinated hydrogel;
   (iii) irradiating at least a portion of the metal-coordinated hydrogel comprising the polyacrylamide-uronate-containing polysaccharide metal-coordinated with the $Fe^{3+}$ metallic cation to reduce the $Fe^{3+}$ metallic cation in the irradiated portion and form a reduced metallic cation in the irradiated portion, thereby creating a patterned hydrogel having a pattern thereon defined by the irradiated portion and a non-irradiated portion of the metal-coordinated hydrogel, wherein the non-irradiated portion comprises the polyacrylamide-uronate-containing polysaccharide metal-coordinated with the $Fe^{3+}$ metallic cation; and
   (iv) rinsing the patterned hydrogel to remove the reduced metallic cation;
   wherein the pattern comprises a variation in elastic moduli and pore size, wherein the irradiated portion has a reduced elastic moduli and a greater pore size than the non-irradiated portion.

2. The method of claim 1, wherein the patterned hydrogel is rinsed with a chelating solution.

3. The method of claim 2, wherein the chelating solution is EDTA.

4. The method of claim 1, wherein the patterned hydrogel is treated with a calcium solution after irradiation.

5. The method of claim 1, wherein the polyacrylamide-uronate-containing polysaccharide is selected from the group consisting of alginate, hyaluronic acid, and pectate.

6. A patterned hydrogel formed by the method of claim 1.

7. A patterned substrate for cell growth formed by the method of claim 1.

8. A patterned substrate for cell differentiation formed by the method of claim 1.

9. A polyacrylamide-uronate-containing polysaccharide hydrogel having a first phase and a second phase, wherein in the first phase the hydrogel is non-irradiated and the polyacrylamide-uronate-containing polysaccharide is metal-coordinated with a $Fe^{3+}$ metallic cation that can be reduced, and wherein in the second phase, the hydrogel has been irradiated and the the polyacrylamide-uronate-containing polysaccharide is metal-coordinated with a $Fe^{3+}$ metallic cation that is in a reduced form.

10. The hydrogel of claim 9, wherein the first and second phase simultaneously occur, each in different portions of the hydrogel.

11. The hydrogel of claim 10, wherein the first and second phase occur in a pattern.

* * * * *

SEQUENCE LISTING

<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Arg Gly Asp Ser
1               5